United States Patent
Stone et al.

(10) Patent No.: US 10,478,159 B2
(45) Date of Patent: *Nov. 19, 2019

(54) BIOPSY NEEDLE DESIGN

(71) Applicant: 3DBiopsy, Inc., Aurora, CO (US)

(72) Inventors: Nelson N. Stone, Vail, CO (US); David Abraham Schechter, Longmont, CO (US); Joshua Kalo Goetz, Broomfield, CO (US); Timothy Patrick Crowley, Arvada, CO (US)

(73) Assignee: 3DBiopsy, Inc., Aurora, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/243,538

(22) Filed: Jan. 9, 2019

(65) Prior Publication Data

US 2019/0175155 A1    Jun. 13, 2019

Related U.S. Application Data

(63) Continuation of application No. 15/605,135, filed on May 25, 2017, now Pat. No. 10,188,422.
(Continued)

(51) Int. Cl.
*A61B 10/02* (2006.01)
*A61B 17/34* (2006.01)
(Continued)

(52) U.S. Cl.
CPC ...... *A61B 10/0233* (2013.01); *A61B 10/0275* (2013.01); *A61B 17/3417* (2013.01);
(Continued)

(58) Field of Classification Search
CPC ............ A61B 10/0233; A61B 10/0275; A61B 10/025; A61B 2010/0208;
(Continued)

(56) References Cited

U.S. PATENT DOCUMENTS 7,063,681 B1    6/2006 Peery
9,149,260 B2   10/2015 Stone et al.
(Continued)

FOREIGN PATENT DOCUMENTS

DE    102013009697    12/2014
WO    2016049676    4/2016

OTHER PUBLICATIONS

Elson N. Stone et al; Deflection Analysis of Different Needle Designs for Prostate Biopsy and Focal Therapy; Technology in Cancer Research & Treatment; 2016; pp. 1-8; tct.sagepub.com.
(Continued)

*Primary Examiner* — Devin B Henson
(74) *Attorney, Agent, or Firm* — Spencer Fane LLP

(57) ABSTRACT

A biopsy needle assembly includes a mandrel within a cannula, the needle assembly is fired into a target tissue to obtain a tissue sample using a force source imparting movement to the needle assembly. The mandrel and cannula design, and force source characteristics minimize needle deflection, and allow the needle assembly to excise extended length tissue samples. The mandrel forms tissue retention ridges within a tissue sample region to reduce fragmentation of the tissue sample.

22 Claims, 24 Drawing Sheets

Related U.S. Application Data

(60) Provisional application No. 62/341,292, filed on May 25, 2016.

(51) Int. Cl.
*A61M 5/32* (2006.01)
*A61M 25/06* (2006.01)

(52) U.S. Cl.
CPC ........ *A61B 17/3421* (2013.01); *A61B 10/025* (2013.01); *A61B 2010/0208* (2013.01); *A61B 2010/0225* (2013.01); *A61M 5/3286* (2013.01); *A61M 25/065* (2013.01)

(58) Field of Classification Search
CPC ............ A61B 2010/0225; A61B 17/34; A61B 17/3417; A61B 17/3421
See application file for complete search history.

(56) References Cited

U.S. PATENT DOCUMENTS

| | | | |
|---|---|---|---|
| 9,610,067 | B2 | 4/2017 | Sekikawa |
| 10,188,422 | B2 * | 1/2019 | Stone ................ A61B 10/0233 |
| 2008/0071193 | A1 | 3/2008 | Reuber et al. |
| 2009/0299220 | A1 | 12/2009 | Field et al. |
| 2013/0102925 | A1 | 4/2013 | McGhie |
| 2014/0236104 | A1 | 8/2014 | Haindl |
| 2015/0230823 | A1 | 8/2015 | Morgan et al. |
| 2016/0361088 | A1 | 12/2016 | MaGuire et al. |

OTHER PUBLICATIONS

N. Stone et al; Deflection Analysis of Different Needle Designs for Transperineal Prostate Biopsy and Focal Therapy; 9th International Symposium on Focal Therapy and Imaging in prostate and kidney cancer; Jun. 23-25, 2016.

Nelson N. Stone, Vladimir Mouraviev, David Schechter, M. Scott Lucia, Elizabeth E. Smith, Paul Arangua, John Hoenemeyer, Jim Rosa, Rajan Bawa, E. David Crawford; The 3DBiopsy Prostate Biopsy System: Preclinical Investigation of a Needle, Actuator and Specimen Collection Device Allowing Sampling of Individualized Prostate Lengths between 20 and 60 mm; Urology (2017), http://dx.doi.org/doi: 10.1016/j.urology.2017.05.046.

* cited by examiner

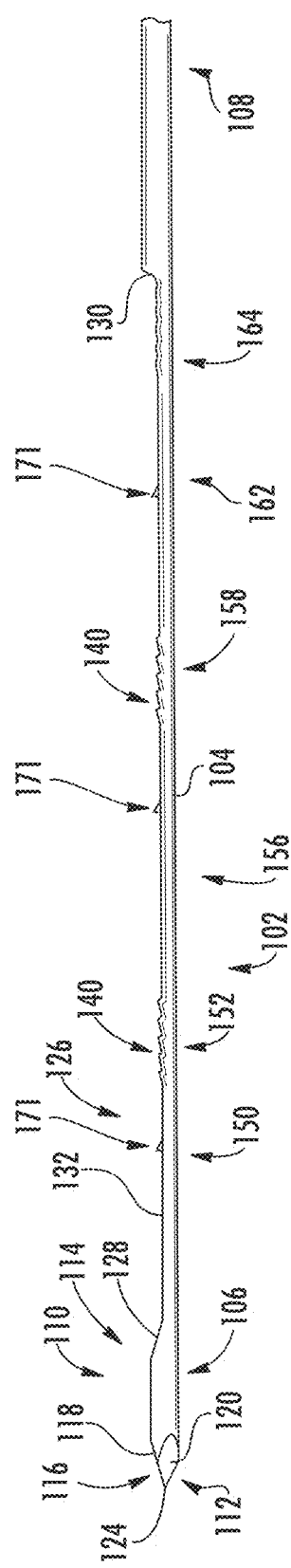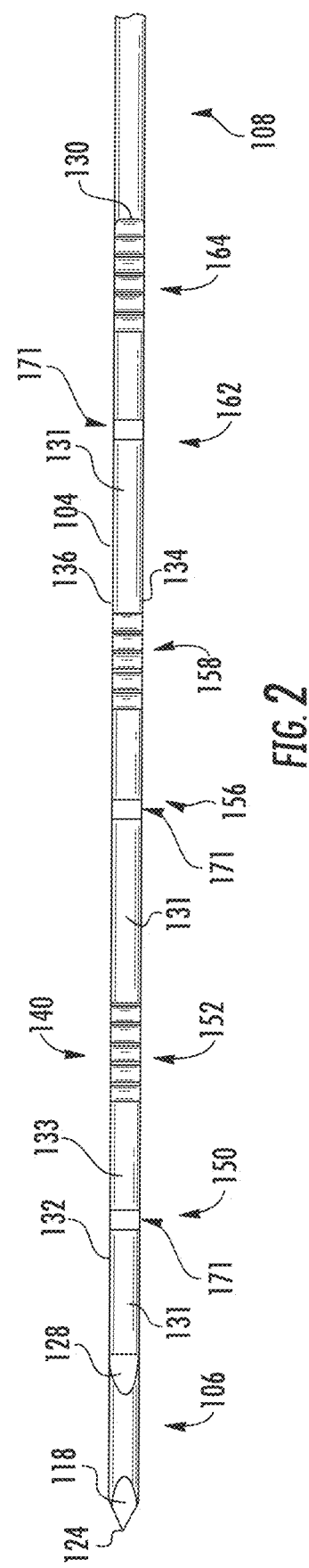

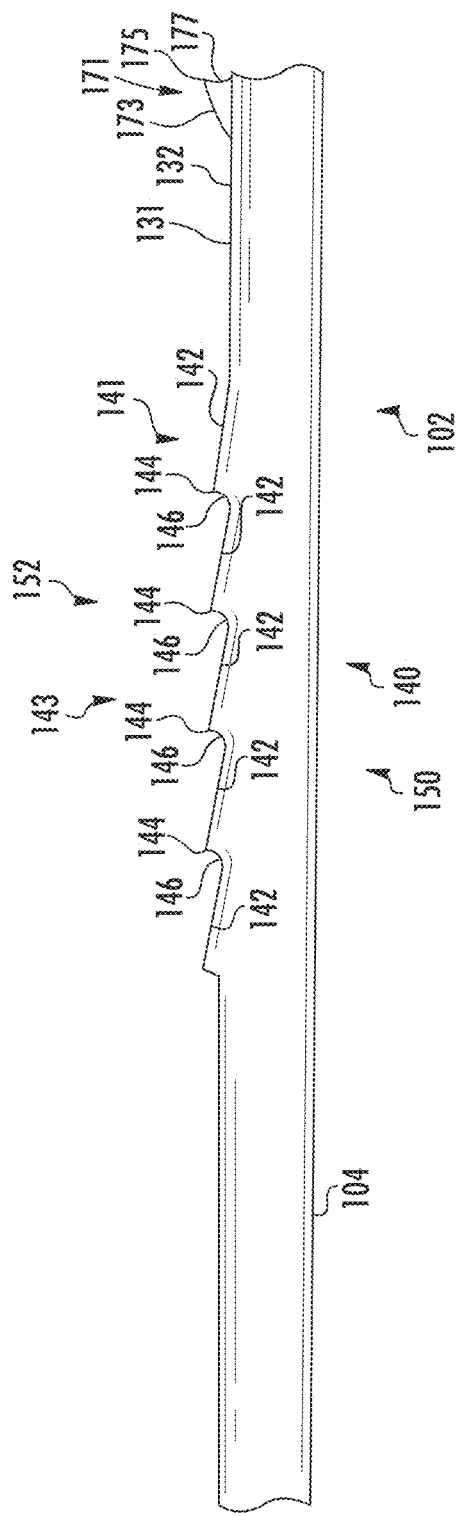

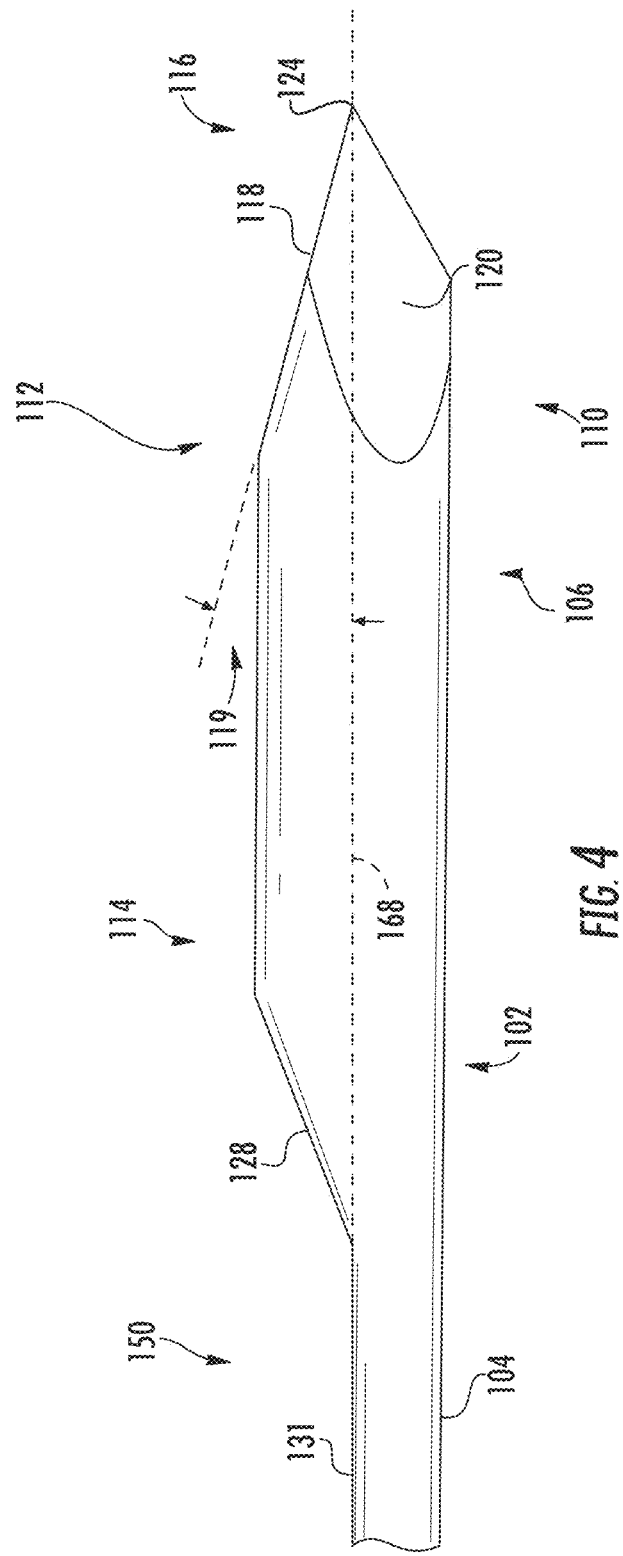

TABLE 1 - DEFLECTION ANALYSIS

| NEEDLE | CANNULA | SPRING # | SPRING RATE (lbs./in) | PRELOAD (lbs.) | SHOT SIZE (mm) | TEST # | DEFLECTION (mm) | DEFLECTION (DEGREES) |
|---|---|---|---|---|---|---|---|---|
| BARD | | N/A | N/A | N/A | 20 | 1 | 0.3 | 0.6 |
| | | | | | | 2 | 1.3 | 2.8 |
| | | | | | | 3 | ND* | ND* |
| | | | | | | 4 | 1.2 | 2.7 |
| | | | | | | 5 | 1.3 | 2.8 |
| | | | | | | 6 | 0.9 | 2.0 |
| | | | | | | 7 | 0.5 | 1.0 |
| | | | | | | 8 | 0.7 | 1.6 |
| | | | | | | 9 | 0.9 | 2.0 |
| | | | | | | 10 | 0.9 | 1.9 |
| LANCET | VET POINT 12° | NEWCOMB CUSTOM | 2 | 2.5 | 20 | 11 | 0 | 0 |
| | | | | | | 12 | 0 | 0 |
| | | | | | | 13 | 0 | 0 |
| | | | | | 40 | 14 | 0.9 | 1.1 |
| | | | | | | 15 | 1.2 | 1.5 |
| | | | | | | 16 | 1.6 | 2.0 |
| | | | | | 60 | 17 | 0.9 | 0.8 |
| | | | | | | 18 | 2.0 | 1.7 |
| | | | | | | 19 | 1.5 | 1.3 |
| TROCAR | VET POINT 12° | NEWCOMB CUSTOM | 2 | 2.5 | 20 | 37 | 0 | 0 |
| | | | | | | 38 | 0 | 0 |
| | | | | | | 39 | 0 | 0 |
| | | | | | 40 | 40 | 0 | 0 |
| | | | | | | 41 | 0 | 0 |
| | | | | | | 42 | 0 | 0 |
| | | | | | 60 | 43 | 1 | 1.0 |
| | | | | | | 44 | 1.3 | 1.1 |
| | | | | | | 45 | 0.0 | 0 |
| | | S-1277 | 3.2 | 3 | 20 | 46 | 0.0 | 0 |
| | | | | | | 47 | 0.0 | 0 |
| | | | | | | 48 | 0.0 | 0 |
| | | | | | 40 | 49 | 0.0 | 0 |
| | | | | | | 50 | 0.0 | 0 |
| | | | | | | 51 | 0.0 | 0 |
| | | | | | 60 | 52 | 1.0 | 0.9 |
| | | | | | | 53 | 0.5 | 0.4 |
| | | | | | | 54 | 1.7 | 1.5 |

*ND-NO DATA RESULTING FROM POOR IMAGE RESOLUTION OR GELATIN BLOCK DISTORTION.

FIG. 20A

TABLE 1- DEFLECTION ANALYSIS (CONT'D)

| NEEDLE | CANNULA | SPRING # | SPRING RATE (lbs./in.) | PRELOAD (lbs.) | SHOT SIZE (mm) | TEST # | DEFLECTION (mm) | DEFLECTION (DEGREES) |
|---|---|---|---|---|---|---|---|---|
| TROCAR | VET POINT 15° | NEWCOMB CUSTOM | 2 | 2.5 | 20 | 55 | 0 | 0 |
| | | | | | | 56 | 0 | 0 |
| | | | | | | 57 | 0 | 0 |
| | | | | | 40 | 58 | 0 | 0 |
| | | | | | | 59 | 0 | 0 |
| | | | | | | 60 | 0 | 0 |
| | | | | | 60 | 61 | 1.4 | 1.2 |
| | | | | | | 62 | 0 | 0 |
| | | | | | | 63 | 0 | 0 |
| | | S-1277 | 3.2 | 3 | 20 | 64 | 0 | 0 |
| | | | | | | 65 | 0 | 0 |
| | | | | | | 66 | 0 | 0 |
| | | | | | 40 | 67 | 0 | 0 |
| | | | | | | 68 | 0 | 0 |
| | | | | | | 69 | 0 | 0 |
| | | | | | 60 | 70 | 0.7 | 0.6 |
| | | | | | | 71 | ND* | ND* |
| | | | | | | 72 | 0.8 | 0.7 |
| TROCAR | VET POINT 20° | NEWCOMB CUSTOM | 2 | 2.5 | 20 | 73 | 0 | 0 |
| | | | | | | 74 | 0 | 0 |
| | | | | | | 75 | 0 | 0 |
| | | | | | 40 | 76 | 0 | 0 |
| | | | | | | 77 | 0 | 0 |
| | | | | | | 78 | 0 | 0 |
| | | | | | 60 | 79 | 0 | 0 |
| | | | | | | 80 | 0 | 0 |
| | | | | | | 81 | 0 | 0 |
| | | S-1277 | 3.2 | 3 | 20 | 82 | 0 | 0 |
| | | | | | | 83 | 0 | 0 |
| | | | | | | 84 | 0 | 0 |
| | | | | | 40 | 85 | 0 | 0 |
| | | | | | | 86 | 0 | 0 |
| | | | | | | 87 | 0 | 0 |
| | | | | | 60 | 88 | 0 | 0 |
| | | | | | | 89 | 1.9 | 1.9 |
| | | | | | | 90 | 2 | 1.7 |

*ND- NO DATA RESULTING FROM POOR IMAGE RESOLUTION OR GELATIN BLOCK DISTORTION.

FIG. 20B

TABLE 3- CORE TEST RESULTS

| NEEDLE | CANNULA SPRING | SPRING RATE (lbs/in) | PRELOAD (lbs) | TARGET SHOT SIZE (mm) | TEST # | ADJUSTED SHOT SIZE (mm) | LENGTH ON NEEDLE (mm) | AVG LENGTH (mm) | STD DEV (mm) | % LENGTH FILL | AVG % LENGTH FILL | AVG AVG % LENGTH FILL | PORCINE KIDNEY # |
|---|---|---|---|---|---|---|---|---|---|---|---|---|---|
| BARD MONOPTY (CATALOG NO. 12160) | | | | 17 | 1 | 17 | 17.0 | 15.9 | 1.2 | 100% | 94% | N/A | 8 |
| | | | | | 2 | | 13.2 | | | 78% | | | |
| | | | | | 3 | | 15.8 | | | 93% | | | |
| | | | | | 4 | | 15.7 | | | 92% | | | |
| | | | | | 5 | | 17.0 | | | 100% | | | |
| | | | | | 6 | | 17.0 | | | 100% | | | |
| | | | | | 7 | | 15.5 | | | 91% | | | |
| | | | | | 8 | | 17.0 | | | 100% | | | |
| | | | | | 9 | | 14.7 | | | 87% | | | |
| | | | | | 10 | | 16.2 | | | 95% | | | |

FIG. 23A

TABLE 3- CORE TEST RESULTS (CONT'D)

| NEEDLE | CANNULA | SPRING | SPRING RATE (lbs./in) | PRELOAD (lbs.) | TARGET SHOT SIZE (mm) | TEST # | ADJUSTED SHOT SIZE (mm) | LENGTH ON NEEDLE (mm) | AVG LENGTH (mm) | STD DEV (mm) | % LENGTH FILL | AVG % LENGTH FILL | AVG AVG % LENGTH FILL | PORCINE KIDNEY # |
|---|---|---|---|---|---|---|---|---|---|---|---|---|---|---|
| 15 G 12 DEG. TROCAR | VET | NEWCOMB | 2 | 2.5 | 20 | 11 | 21.2 | 21.8 | 18.7 | 1.3 | 103% | 88% | 92% | 6 |
| | | | | | | 12 | | 17.5 | | | 82% | | | |
| | | | | | | 13 | | 17.8 | | | 84% | | | |
| | | | | | | 14 | | 17.9 | | | 84% | | | |
| | | | | | | 15 | | 18.5 | | | 87% | | | |
| | | | | | | 16 | | 19.1 | | | 90% | | | |
| | | | | | | 17 | | 20.0 | | | 94% | | | |
| | | | | | | 18 | | 17.2 | | | 81% | | | |
| | | | | | | 19 | | 18.9 | | | 89% | | | |
| | | | | | | 20 | | 18.8 | | | 89% | | | |
| | | | | | 40 | 21 | 44.3 | 45.6 | 42.6 | 2.2 | 103% | 96% | | |
| | | | | | | 22 | | 40.7 | | | 92% | | | |
| | | | | | | 23 | | 41.5 | | | 94% | | | |
| | | | | | | 24 | | 44.2 | | | 100% | | | |
| | | | | | | 25 | | 41.1 | | | 93% | | | |
| | | | | | | 26 | | 44.3 | | | 100% | | | |
| | | | | | | 27 | | 41.0 | | | 93% | | | |
| | | | | | | 28 | | 46.3 | | | 105% | | | |
| | | | | | | 29 | | 39.6 | | | 89% | | | |
| | | | | | | 30 | | 41.9 | | | 95% | | | |
| | | | | | 60 | 31 | 60 | 51.4 | 54 | 2.9 | 86% | 90% | | |
| | | | | | | 32 | | 56.9 | | | 95% | | | |
| | | | | | | 33 | | 58.3 | | | 97% | | | |
| | | | | | | 34 | | 59.0 | | | 98% | | | |
| | | | | | | 35 | | 51.9 | | | 86% | | | |
| | | | | | | 36 | | 50.7 | | | 84% | | | |
| | | | | | | 37 | | 54.7 | | | 91% | | | |
| | | | | | | 38 | | 52.5 | | | 87% | | | |
| | | | | | | 39 | | 51.0 | | | 85% | | | |
| | | | | | | 40 | | 53.9 | | | 90% | | | |

TABLE 3- CORE TEST RESULTS (CONT'D)

| NEEDLE | CANNULA | SPRING | SPRING RATE (lbs./in) | PRELOAD (lbs.) | TARGET SHOT SIZE (mm) | TEST # | ADJUSTED SHOT SIZE (mm) | LENGTH ON NEEDLE (mm) | AVG LENGTH (mm) | STD DEV (mm) | % LENGTH FILL | AVG % LENGTH FILL | AVG AVG % LENGTH FILL | PORCINE KIDNEY # |
|---|---|---|---|---|---|---|---|---|---|---|---|---|---|---|
| 15 G TROCAR | 12 DEG VET | S-1277 | 3.2 | 3 | 20 | 41 | 23.5 | 17.3 | 19.4 | 2.2 | 74% | 82% | 89% | 7 |
| | | | | | | 42 | | 21.7 | | | 92% | | | |
| | | | | | | 43 | | 23.9 | | | 102% | | | |
| | | | | | | 44 | | 17.7 | | | 75% | | | |
| | | | | | | 45 | | 19.3 | | | 82% | | | |
| | | | | | | 46 | | 18.5 | | | 79% | | | |
| | | | | | | 47 | | 19.6 | | | 83% | | | |
| | | | | | | 48 | | 15.8 | | | 67% | | | |
| | | | | | | 49 | | 20.6 | | | 88% | | | |
| | | | | | | 50 | | 19.3 | | | 82% | | | |
| | | | | | 40 | 51 | 41.2 | 42.6 | 37.4 | 3.7 | 103% | 91% | | |
| | | | | | | 52 | | 41.0 | | | 100% | | | |
| | | | | | | 53 | | 37.9 | | | 92% | | | |
| | | | | | | 54 | | 36.5 | | | 89% | | | |
| | | | | | | 55 | | 37.6 | | | 91% | | | |
| | | | | | | 56 | | 38.1 | | | 92% | | | |
| | | | | | | 57 | | 33.8 | | | 82% | | | |
| | | | | | | 58 | | 28.5 | | | 69% | | | |
| | | | | | | 59 | | 38.7 | | | 94% | | | |
| | | | | | | 60 | | 38.9 | | | 94% | | | |
| | | | | | 60 | 61 | 60 | 58.4 | 57.1 | 2.1 | 97% | 95% | | |
| | | | | | | 62 | | 58.2 | | | 97% | | | |
| | | | | | | 63 | | 58.7 | | | 98% | | | |
| | | | | | | 64 | | 59.3 | | | 99% | | | |
| | | | | | | 65 | | 58.7 | | | 98% | | | |
| | | | | | | 66 | | 57.5 | | | 96% | | | |
| | | | | | | 67 | | 56.7 | | | 94% | | | |
| | | | | | | 68 | | 56.3 | | | 94% | | | |
| | | | | | | 69 | | 52.3 | | | 87% | | | |
| | | | | | | 70 | | 54.6 | | | 91% | | | |

FIG. 23D

TABLE 3- CORE TEST RESULTS (CONT'D)

| NEEDLE | CANNULA | SPRING | SPRING RATE (lbs./in) | PRELAOD (lbs.) | TARGET SHOT SIZE (mm) | TEST # | ADJUSTED SHOT SIZE (mm) | LENGTH ON NEEDLE (mm) | AVG LENGTH (mm) | STD DEV (mm) | % LENGTH FILL | AVG % LENGTH FILL | AVG AVG % LENGTH FILL | PORCINE KIDNEY # |
|---|---|---|---|---|---|---|---|---|---|---|---|---|---|---|
| 15 G TROCAR | 20 DEG. MENGHINI | NEWCOMB | 2 | 2.5 | 20 | 71 | 18.3 | 11.3 | 15.1 | 2.3 | 62% | 82% | 86% | 5 |
| | | | | | | 72 | | 15.9 | | | 87% | | | |
| | | | | | | 73 | | 15.5 | | | 84% | | | |
| | | | | | | 74 | | 16.6 | | | 90% | | | |
| | | | | | | 75 | | 12.8 | | | 70% | | | |
| | | | | | | 76 | | 16.2 | | | 88% | | | |
| | | | | | | 77 | | 15.8 | | | 86% | | | |
| | | | | | | 78 | | 18.0 | | | 98% | | | |
| | | | | | | 79 | | 11.5 | | | 63% | | | |
| | | | | | | 80 | | 17.5 | | | 95% | | | |
| | | | | | 40 | 81 | 40 | 33.8 | 35.4 | 3 | 85% | 89% | | |
| | | | | | | 82 | | 34.9 | | | 87% | | | |
| | | | | | | 83 | | 37.0 | | | 93% | | | |
| | | | | | | 84 | | 39.4 | | | 99% | | | |
| | | | | | | 85 | | 36.9 | | | 92% | | | |
| | | | | | | 86 | | 35.9 | | | 90% | | | |
| | | | | | | 87 | | 39.0 | | | 98% | | | |
| | | | | | | 88 | | 28.1 | | | 70% | | | |
| | | | | | | 89 | | 35.1 | | | 88% | | | |
| | | | | | | 90 | | 34.2 | | | 86% | | | |
| | | | | | 60 | 91 | 56.3 | 41.3 | 49.1 | 6.2 | 73% | 87% | | 4 |
| | | | | | | 92 | | 40.1 | | | 71% | | | |
| | | | | | | 93 | | 40.7 | | | 72% | | | |
| | | | | | | 94 | | 47.0 | | | 83% | | | |
| | | | | | | 95 | | 55.4 | | | 98% | | | |
| | | | | | | 96 | | 56.3 | | | 100% | | | |
| | | | | | | 97 | | 56.1 | | | 100% | | | |
| | | | | | | 98 | | 52.4 | | | 93% | | | |
| | | | | | | 99 | | 53.5 | | | 95% | | | |
| | | | | | | 100 | | 48.1 | | | 85% | | | |

FIG. 23E

TABLE 3- CORE TEST RESULTS (CONT'D)

| NEEDLE | CANNULA | SPRING | SPRING RATE (lbs./in) | PRELOAD (lbs.) | TARGET SHOT SIZE (mm) | TEST # | ADJUSTED SHOT SIZE (mm) | LENGTH ON NEEDLE (mm) | AVG LENGTH (mm) | STD DEV (mm) | % LENGTH FILL | AVG% LENGTH FILL | AVG AVG % LENGTH FILL | PORCINE KIDNEY # |
|---|---|---|---|---|---|---|---|---|---|---|---|---|---|---|
| 15 G TROCAR | 20 DEG. MENGHINI | S-1277 | 3.2 | 3 | 20 | 101 | 20.3 | 22.1 | 18.9 | 3 | 109% | 93% | 84% | 3 |
| | | | | | | 102 | | 22.8 | | | 112% | | | |
| | | | | | | 103 | | 19.6 | | | 97% | | | |
| | | | | | | 104 | | 17.4 | | | 86% | | | |
| | | | | | | 105 | | 15.2 | | | 75% | | | |
| | | | | | | 106 | | 20.6 | | | 101% | | | |
| | | | | | | 107 | | 17.7 | | | 87% | | | |
| | | | | | | 108 | | 14.7 | | | 72% | | | |
| | | | | | | 109 | | 23.1 | | | 114% | | | |
| | | | | | | 110 | | 16.1 | | | 79% | | | |
| | | | | | 40 | 111 | 40.8 | 29.7 | 32.7 | 3.1 | 73% | 80% | | 2 |
| | | | | | | 112 | | 29.0 | | | 71% | | | |
| | | | | | | 113 | | 29.0 | | | 71% | | | |
| | | | | | | 114 | | 35.8 | | | 88% | | | |
| | | | | | | 115 | | 30.5 | | | 75% | | | |
| | | | | | | 116 | | 31.7 | | | 78% | | | |
| | | | | | | 117 | | 32.0 | | | 78% | | | |
| | | | | | | 118 | | 36.6 | | | 90% | | | |
| | | | | | | 119 | | 36.1 | | | 88% | | | |
| | | | | | | 120 | | 36.8 | | | 90% | | | |
| | | | | | 60 | 121 | 60 | 51.9 | 47.3 | 2.9 | 86% | 79% | | 1 |
| | | | | | | 122 | | 46.3 | | | 77% | | | |
| | | | | | | 123 | | 48.1 | | | 80% | | | |
| | | | | | | 124 | | 41.5 | | | 69% | | | |
| | | | | | | 125 | | 49.0 | | | 82% | | | |
| | | | | | | 126 | | 48.1 | | | 80% | | | |
| | | | | | | 127 | | 49.9 | | | 83% | | | |
| | | | | | | 128 | | 47.4 | | | 79% | | | |
| | | | | | | 129 | | 48.0 | | | 80% | | | |
| | | | | | | 130 | | 43.1 | | | 72% | | | |

BIOPSY NEEDLE DESIGN

CROSS-REFERENCE TO RELATED APPLICATIONS

This application in a continuation of U.S. Non-Provisional patent application Ser. No. 15/605,135, filed May 25, 2017, which claims priority in U.S. Provisional Application No. 62/341,292, filed May 25, 2016, entitled Biopsy Needle Design, the contents of which are hereby incorporated by reference.

BACKGROUND

1. Field of the Disclosed Subject Matter

The disclosed subject matter relates to biopsy needle designs and functional characteristics, and more particularly to a mandrel and cannula tip design that minimizes deflection during use, and translational force characteristics acting on the mandrel and cannula allowing extended biopsy core samples of target tissues and improved lesion localization for targeted focal therapy.

2. Description of the Background Art

Predicate biopsy needles and devices used to excise tissue samples from target tissues result in low quality tissue core samples. The short length of core samples, and fragmented characteristic of the core samples inhibits accurate determination of the size, location, and extent of lesions. Excising extended length tissue core samples with current technologies results in significant deflection of the biopsy needle introducing additional error into tissue sampling. Accurately sampling tissues is important for accurately identifying the location and extent of tissue disease, and effective planning of targeted focal therapy.

SUMMARY

An embodiment of the disclosed subject matter includes a cannula, a mandrel, and a cannula force source. The cannula has a tubular body extending between a first end and a second end, the tubular body having a first side and an opposite second side. The cannula forms a leading edge formed at the first end, the leading edge extends along a first plane, the first plane extends between the first side and second side, the first plane forms a leading edge angle between the intersection of the first side and the first plane, and the leading edge angle is between approximately 12 degrees and approximately 20 degrees. The mandrel has a body extending between a first end and a second end, a trocar point formed by the first end, a notch formed by the body, the notch forms a bed extending between the first end and the second end, and a first sample region is formed by the bed. The first sample region includes a first plurality of ridges. Each of the first plurality of ridges includes a flank extending from the bed toward the second end, the flank terminates at a crest. The cannula force source imparts movement to the cannula having a loaded force between approximately 7 lbs. to approximately 11 lbs.

In an aspect of the embodiment, the leading edge angle is 12 degrees, and the loaded force is approximately 7.32 lbs. In an aspect, the cannula force source is a compression spring. In an aspect, a second sample region is formed by the bed, the second sample region includes a second plurality of ridges, and a deck disposed between the first plurality of ridges and the second plurality of ridges. Each of the second plurality of ridges includes a flank extending from the bed toward the second end, the flank terminates in a crest, and a concave slope descends from the crest. In an aspect, the cannula force source imparts between approximately 2 lbs./in to approximately 3.2 lbs./in upon the cannula. In an aspect, the mandrel force source moves the mandrel between approximately 1 mm and approximately 66 mm. In an aspect, a mandrel force source imparts movement to the mandrel of a loaded force between approximately 7 lbs. to approximately 11 lbs. In an aspect, the mandrel force source is a compression spring. In an aspect, the leading edge angle is 20 degrees, and the loaded force is approximately 7.32 lbs. In an aspect, the bed includes a reverse ridge, the reverse ridge includes a flank extending from the bed toward the first end, the flank terminates at a crest, and a concave slope descends from the crest.

An embodiment of the disclosed subject matter includes a cannula, a mandrel, a cannula spring, and a mandrel spring. The cannula includes a tubular body extending between a first end and a second end, the tubular body having a first side and a second side, and a vet point formed at the first end. The vet point includes a leading edge extending along a first plane, the first plane extending between the first side and second side, the plane forming a leading edge angle between the intersection of the first side and the first plane, and the leading edge angle is 12 degrees. The mandrel includes a body extending between a first end and a second end along a central longitudinal axis, and a trocar point formed by the first end. The trocar point includes a first beveled surface forming a first bevel angle between the intersection of the first beveled surface and the central longitudinal axis, and the first bevel angle is 15 degrees. The cannula spring imparts movement to the cannula having a loaded force of approximately 7.32 lbs. The mandrel spring imparts movement to the mandrel having a loaded force of approximately 7.32 lbs. And an actuator houses the cannula spring and mandrel spring.

In an aspect of the embodiment, the mandrel includes a notch and a first sample region. The notch is formed by the body, the notch forms a bed extending between the first end and the second end. The first sample region includes a deck disposed between the notch first end and a first plurality of ridges. Each ridge includes a flank extending from the bed toward the second end, the flank terminates at a crest, and a concave slope descends from the crest. In an aspect, the bed includes a reverse ridge. The reverse ridge includes a flank extending from the bed toward the first end, the flank terminates at a crest, and a concave slope descends from the crest. In an aspect, the mandrel spring moves the mandrel between approximately 1 mm and approximately 66 mm. In an aspect, the cannula spring and mandrel spring are compression springs.

An embodiment of the disclosed subject matter includes a cannula, a mandrel, a cannula spring, and a mandrel spring. The cannula includes a tubular body extending between a first end and a second end, the tubular body having a first side and a second side, a vet point formed at the first end, the vet point includes a leading edge extending along a first plane, the first plane extends between the first side and second side, the plane forms a leading edge angle between the intersection of the first side and the first plane, and the leading edge angle is 20 degrees. The mandrel includes a body extending between a first end and a second end along a central longitudinal axis, a trocar point is formed by the first end, the trocar point includes a first beveled surface forming first bevel angle between the intersection of the first beveled surface and the central longitudinal axis, and the first bevel angle is 15 degrees. The cannula spring imparts movement to the cannula, the cannula spring includes a spring rate of approximately 2 lbs./in., and a loaded force of approximately 7.32 lbs. The mandrel spring imparts movement to the mandrel, the mandrel spring includes a spring rate of approximately 2 lbs./in., and a loaded force of approximately 7.32 lbs. And an actuator houses the cannula spring and mandrel spring.

In an aspect of the embodiment, the mandrel includes a notch, a first sample region, and a reverse ridge. The notch is formed by the body, the notch forms a bed extending between the first end and the second end. The first sample region includes a deck disposed between the notch first end and a first plurality of ridges. Each ridge includes a flank extending from the bed toward the second end, the flank terminates at a crest, and a concave slope descends from the crest. The reverse ridge includes a flank extending from the bed toward the first end, the flank terminates at a crest. In an aspect, the bed includes a reverse ridge, the reverse ridge includes a flank extending from the bed toward the first end, the flank terminates at a crest, and a concave slope descends from the crest. In an aspect, the mandrel spring moves the mandrel between approximately 1 mm and approximately 66 mm. In an aspect, the cannula spring and mandrel spring are compression springs.

An embodiment of the disclosed subject matter includes a cannula assembly, a mandrel assembly, and a cannula force source. The cannula assembly translates in a first direction and includes a tubular body extending between a first end and a second end, the tubular body has a first side and an opposite second side, and a leading edge formed at the first end, the leading edge extends along a first plane, the first plane extends between the first side and second side, the first plane forms a leading edge angle between the intersection of the first side and the first plane, and the leading edge angle is between approximately 12 degrees and approximately 20 degrees. The mandrel assembly includes a body extending between a first end and a second end, a trocar point formed by the first end, and a notch formed by the body, the notch forming a bed extending between the first end and the second end. The cannula force source imparts movement to the cannula assembly, and the cannula assembly includes a momentum between approximately 0.099 kg m/s to approximately 0.256 kg m/s in the first direction.

In an aspect, the cannula assembly momentum is between approximately 0.150 kg m/s to approximately 0.217 kg m/s in the first direction. In an aspect, a first sample region is formed by the bed, the first sample region includes a first plurality of ridges, wherein each of the first plurality of ridges includes a flank extending from the bed toward the second end, the flank terminates at a crest, and a concave slope descends from the crest. In an aspect, the first sample region further includes a reverse ridge, the reverse ridge includes a flank extending from the bed toward the first end, and the flank terminates at a crest. In an aspect, the mandrel assembly translates in the first direction, and a mandrel force source imparts movement to the mandrel assembly, and the mandrel assembly includes a momentum between approximately 0.120 kg m/s to approximately 0.282 kg m/s in the first direction. In an aspect, the mandrel assembly momentum is between approximately 0.165 kg m/s to approximately 0.239 kg m/s in the first direction.

BRIEF DESCRIPTION OF THE DRAWINGS

The present disclosed subject matter is described herein with reference to the following drawing figures, with greater emphasis being placed on clarity rather than scale:

FIG. 1 is an elevation view of a mandrel embodying features of the disclosed subject matter.

FIG. 2 is a plan view of the mandrel of FIG. 1.

FIG. 3 is an enlarged elevation view of the ridges of the mandrel of FIG. 1.

FIG. 4 is an enlarged elevation view of the point of the mandrel of FIG. 1.

FIGS. 20A-20B is a table of data from the deflection analysis of Example 1.

FIGS. 23A-23E is a table of data from the deflection analysis of Example 2.

DETAILED DESCRIPTION

Figure 5:
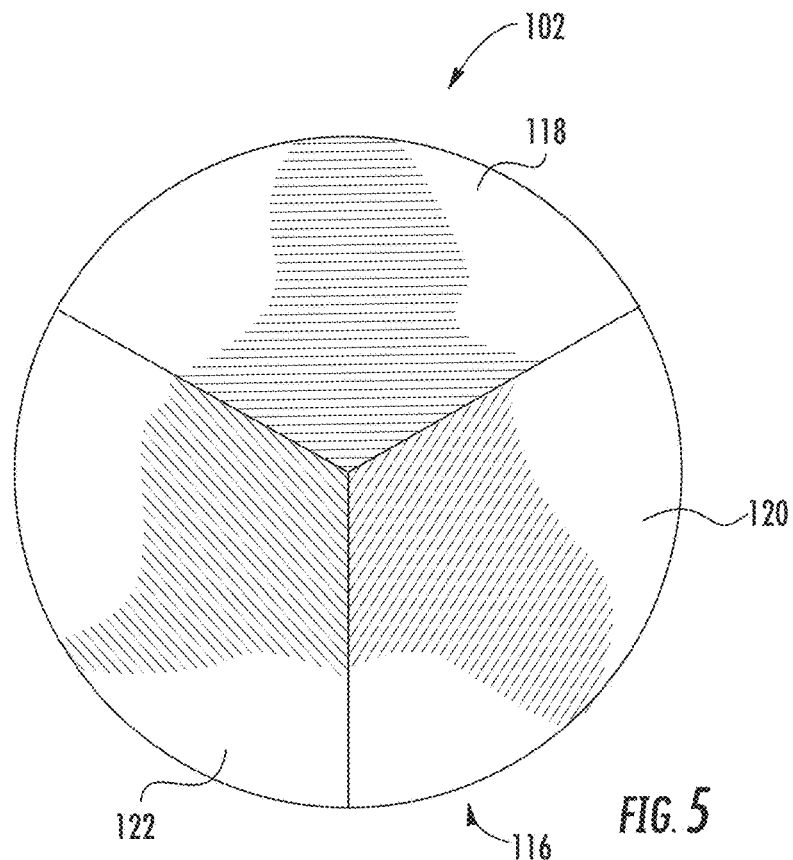
FIG. 5 is an end view of the point of the mandrel of FIG. 1.
Figure 6:
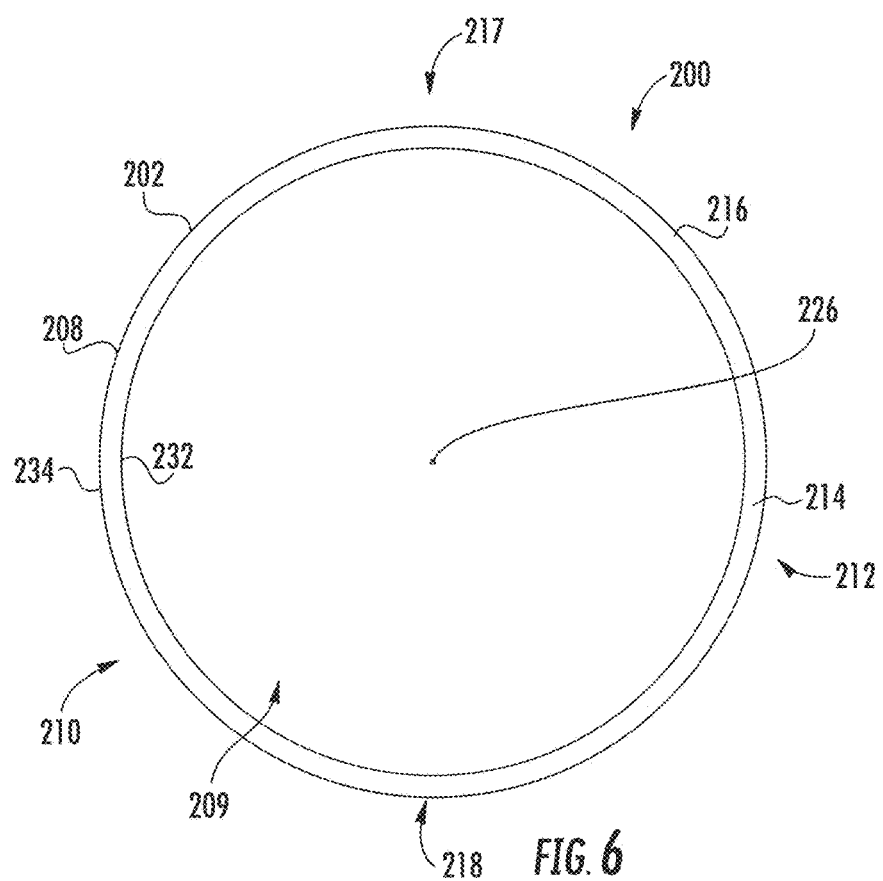
FIG. 6 is an end view of a cannula embodying features of the disclosed subject matter.
Figure 7:
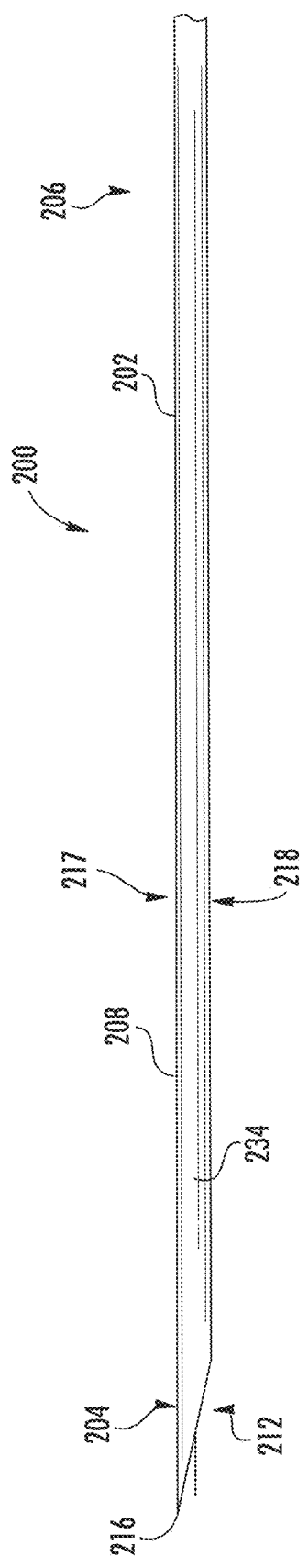
FIG. 7 is an elevation view of a cannula embodying features of the disclosed subject matter.
Figure 8:
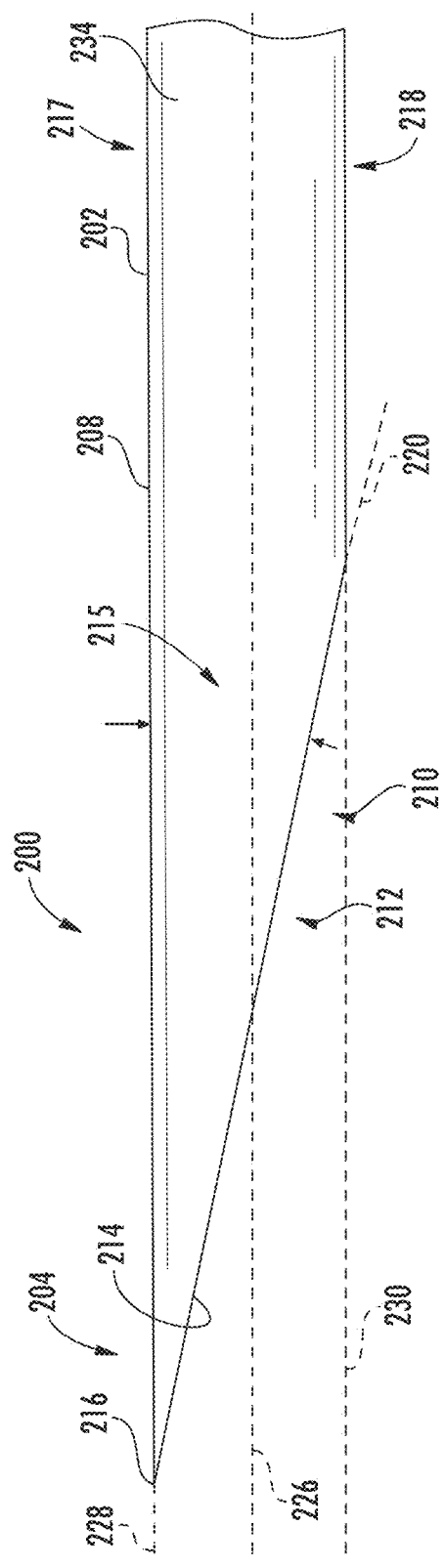
FIG. 8 is an enlarged elevation view of the tip of the cannula of FIG. 7.
Figure 9:
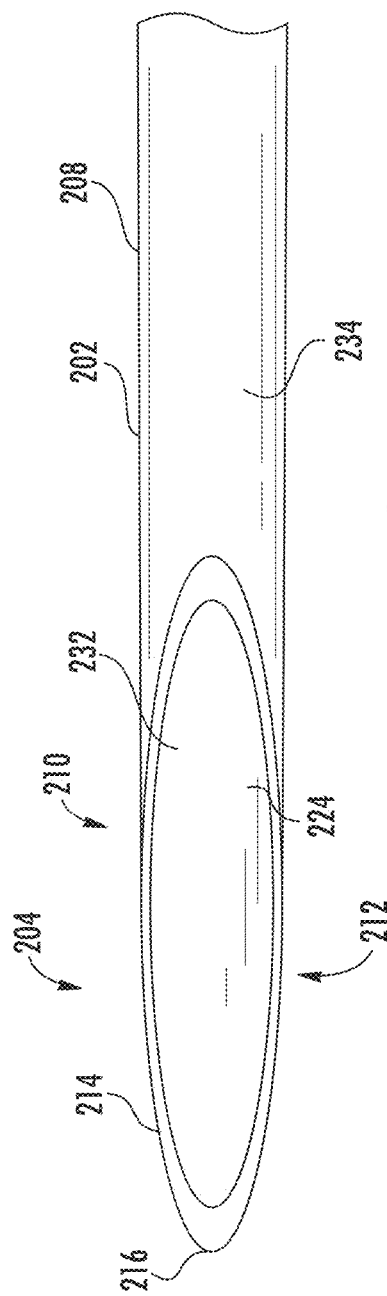
FIG. 9 is an enlarged bottom view of the tip of the cannula of FIG. 7.

The needle assembly 100 and translational force characteristics of the disclosed subject matter includes design and functional characteristics that minimize needle deflection during use, increasing the accuracy and amount of tissue sampled and improving the effectiveness of planning and administration of targeted focal therapy. Embodiments of the needle assembly 100 and translational force characteristics are shown in the drawing figures, and are disclosed in the following detailed description and claims. Referring to the drawings, FIGS. 1-12 show a needle assembly 100 with a mandrel 102 that moves within a cannula 200 forming a biopsy needle assembly. A combination of the mandrel 102 point 116 design, cannula 200 tip 212 design, and translational force characteristics provide for accurate excision of extended length biopsy core samples of target tissues to facilitate disease diagnosis and planning.

The mandrel 102 has design characteristics that aid in accurate placement of the mandrel 102 within a target tissue, and retention of tissue within the tissue sample notch 126. Referring to FIGS. 1-4, the mandrel 102 has an elongated body 104 along a central longitudinal axis 168 extending between a distal or first end 106 and a proximal or second end 108. The mandrel 102 is made from a resilient material. In an implementation, the flexural modulus of the resilient material is greater than 29,000 ksi (205 MPa). In an implementation, the resilient material is metal. In an implementation, the metal is an alloy of cobalt chromium, or an alloy of cobalt and nickel such as MP35N, or an alloy formulated to increase flexural modulus greater than stainless steel. In an implementation, the mandrel 102 is a 15 gauge needle. In an implementation, the mandrel 102 is a 17 gauge needle. In an implementation, the mandrel 102 is a 19 gauge needle. The first end 106 forms a cylindrical end 110 with a first portion 112 and second portion 114. The first portion 112 forms a trocar point 116 with a first beveled surface 118, an adjacent second beveled surface 120, and a third beveled surface 122. The second end portion 114 tapers toward the second end 108 from a cylindrical cross-section to a semicircular cross section forming a first end 128 of the notch 126.

Referring to FIGS. 4-5, the first, second, and third beveled surfaces 118, 120, and 122 intersect at the central longitudinal axis 168 forming a tip 124. The first beveled surface 118 forms a first beveled angle 119 between the intersection of the first beveled surface 118 and the central longitudinal axis 168. The second beveled surface 120 forms a second beveled angle between the intersection of the second beveled surface 120 and the central longitudinal axis 168, and the third beveled surface 122 forms a third beveled angle between the intersection of the third beveled surface 122 and the central longitudinal axis 168. In an implementation, each of the first beveled surface 118, second beveled surface 120, and third beveled surface 122 form an approximately 15 degree angle with the central longitudinal axis, with the intersection of the first beveled surface 118 and the third beveled surface 122 located 120 degrees from the intersection of the first beveled surface 118 and the second beveled surface 120, and located 120 degrees from the intersection of the second beveled surface 120 and the third beveled surface 122.

The body 104 forms a tissue retaining notch 126 with a lower surface or bed 132 between the first end 106 and second end 108. The body 104 beneath the bed 132 has a generally semicircular cross-section with a face 133 extending between the second portion 114 and second end 108. The bed 132 has a length extending longitudinally between a first end 128 and a second end 130, and a width extending laterally between a first longitudinal edge 134 and a second longitudinal edge 136. The notch 126 generally forms three tissue sample regions each having a deck at a distal portion and grip elements at a proximal portion. The grip elements aid in retaining a biopsy tissue sample within the notch 126 as the cannula 200 tip 212 moves toward the mandrel 102 first end 106 passing over the sample regions and cutting the tissue sample from a target tissue.

In an embodiment, the notch 126 extends a length of the body 104 longitudinally between approximately 6 mm from the tip 124 to approximately 66 mm from the tip 124, forming a 60 mm bed 132. In an implementation, the notch bed 132 forms a first sample region 150, a second sample region 156, and a third sample region 162. The first sample region 150 extends from the first end 128 toward the second end 108 approximately 20 mm longitudinally along the bed 132 forming a deck 131 terminating in a first grip section 152. The first grip section 152 consists of a plurality of ridges 140. The plurality of ridges 140 include a primary ridge 141 followed by secondary ridges 143. Referring to FIG. 3, each ridge 140 is formed by a flank 142 extending from the bed 132 toward the second end 108 terminating at a crest 144, and a rear concave slope 146 descending from the crest 144. The flank 142 of the primary ridge 141 originates at the deck 131. The flank 142 of the secondary ridges 143 originates at the base of the concave slope 146 of the immediately distal ridge 140. The second sample region 156 extends from the proximal end of the first grip section 152 towards the second end 108 approximately 20 mm longitudinally along the bed 132 forming a deck 131 terminating in a second grip section 158. The second grip section 158 consists of a plurality of ridges 140 comprising a primary ridge 141 followed by secondary ridges 143. The third sample region 162 extends from the proximal end of the second grip section 158 toward the second end 108 approximately 20 mm longitudinally along the bed 132 forming a deck 131 terminating in a third grip section 164. As with the second grip section 158, the third grip section 164 consists of a plurality of ridges 140 comprising a primary ridge 141 followed by secondary ridges 143, with the terminal secondary ridge 143 disposed adjacent the second end 130. Operation of the mandrel 102 in conjunction with the cannula 200 removes a tissue sample from a target tissue.

In an embodiment, the deck includes one or more reverse grip elements that aid in retaining the biopsy tissue sample within the notch 126 as the cannula 200 tip 212 moves toward the mandrel 102 second end 108 exposing the tissue sample within the notch 126. The reverse grip elements include one or more reverse ridges 171 having a flank 173 extending from the bed 132 toward the first end 106 terminating at a crest 175, and a front concave slope 177 descending from the crest 175. Accordingly, each deck 131 adjacent the first, second, and third grip sections 152, 158, and 164 may optionally include one or more reverse ridges 171.

Referring to FIGS. 6-9, the cannula 200 has an elongated tubular bore 209 extending along a central longitudinal axis 226 surrounded by a sidewall 208 forming a tubular body 202. The sidewall 208 has an interior surface 232 and an exterior surface 234. A first side 217 of the body 202 forms a major longitudinal axis 228 parallel to the central longitudinal axis 226, and an opposite second side 218 of the body 202 forms a minor longitudinal axis 230 parallel to the central longitudinal axis 226. The tubular body 202 has an inner circumferential diameter allowing the mandrel 102 to be slideably received therein, thereby allowing the cannula 200 to cut tissue as it slides over the mandrel 102, such as in conventional biopsy needle assemblies. The body extends between a distal or first end 204 forming a tip 212, and a proximal or second end 206. The body 202 forms a bore 209 opening 210 extending between the first end 204 and an opposite second end 206. In an embodiment, the tip 212 forms a vet-point. In an implementation, the tip 212 forms a leading edge 214 and a cutting edge 216. The leading edge 214 is along a first plane 220. The first plane 220 begins at the first side 217 and extends proximally toward the second side 218 forming a leading edge angle 215 between the intersection of the first plane 220 and the major longitudinal axis 228. The leading edge 214 angle 215 is between approximately 12 degrees and 20 degrees. In an implementation, the leading edge 214 angle 215 is approximately 12 degrees. In an implementation, the leading edge 214 angle 215 is approximately 15 degrees. In another implantation, the leading edge 214 angle 215 is approximately 20 degrees. The tip 212 is at the major longitudinal axis 228 adjacent opening 210.

In use, a mandrel 102 is slideably fitted within a complimentary cannula 200, with the mandrel 102 point 116 protruding from the cannula 200 first end 204, and the bed 132 facing the major longitudinal axis 228. The needle assembly 100 is positioned in an actuator assembly and each needle is sequentially moved by a force source to obtain a tissue sample from a target tissue 252. In an implementation, the mandrel 102 is pushed or fired in a first direction into the target tissue first, exposing a sample region to a tissue sample. The sample region extending beyond the tip 212 of the cannula 200 determines the length and volume of the tissue sample excised by the needle assembly 100. Next, the cannula 200 is pushed or fired in the first direction into the target tissue, over the sample region, encapsulating a tissue sample 254 between the mandrel 102 and cannula 200. In an implementation, the sample region is between approximately 1 mm and approximately 60 mm in length.

Figure 10:
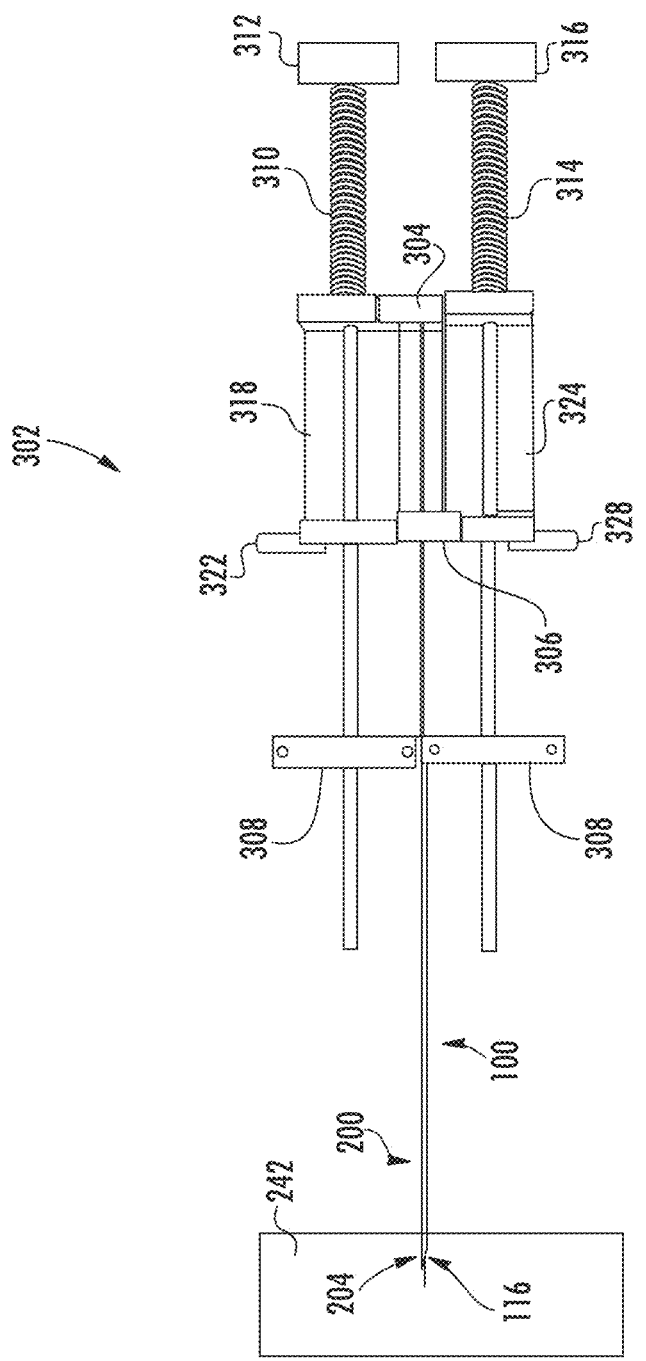
FIG. 10 is a plan view of an exemplary actuator assembly.
Figure 11:
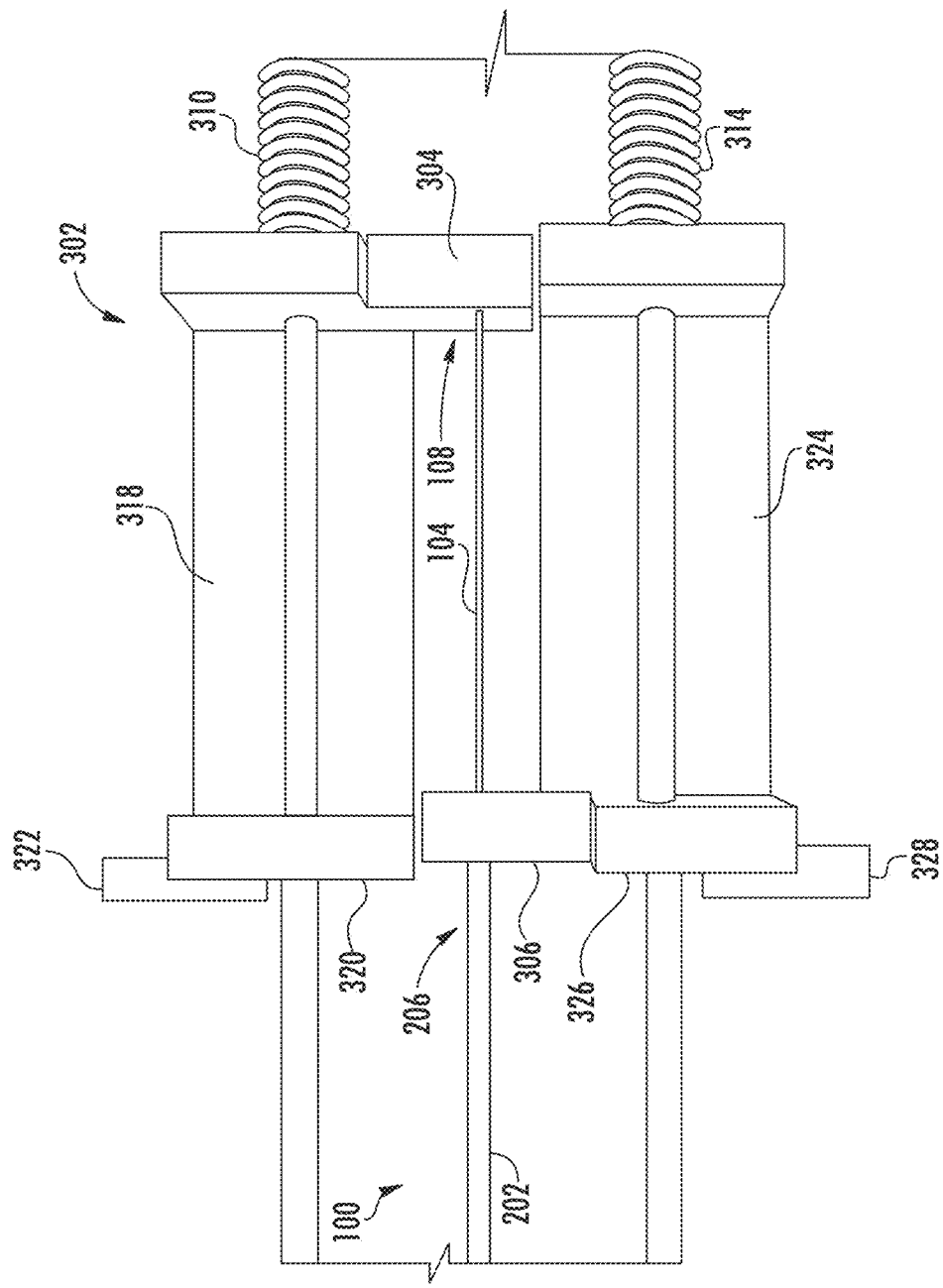
FIG. 11 is an enlarged plan view of the exemplary actuator assembly of FIG. 10.

The actuator assembly generally includes a first force source imparting a translational motion to the mandrel 102, and a second force source imparting a translational motion to the cannula 200. Referring to FIGS. 10-11, an exemplary actuator assembly 302 includes a stop 308 with a mandrel carrier 304 connected to a mandrel mount 318 movably disposed between the stop 308 and a first contact 312, and a cannula carrier 306 connected to a cannula mount 324 movably disposed between the stop 308 and a second contact 316. A general representation of an actuator assembly 302 is shown and described approximating the features of needle actuators, but the features of the disclosed actuator assembly 302 may be embodied in different structural forms, such as biopsy needle guns housing the force sources and supporting the mandrel and cannula during firing. The mandrel 102 is operably connected to the mandrel carrier 304 by the mandrel mount 318 forming a mandrel assembly, and the cannula 200 is operably connected to the cannula carrier 306 by the cannula mount 324 forming a cannula assembly. The mandrel 102 and cannula 200 can be modified to be used with any appropriately designed actuator assembly.

In an embodiment, the force sources are resilient members, such as a helical spring. The helical spring may be an extension spring, or a compression spring. In an implementation, the helical spring has a spring rate between approximately 2 lbs./in. and 3.2 lbs./in. In an implementation, a helical mandrel spring 310 is positioned whereby one end is operably connected to the first contact 312 and the opposite end is operably connected to the mandrel mount 318 and provides the first force source upon releasing compression, and a helical cannula spring 314 is positioned whereby one end is operably connected to the second contact 316 and the opposite end is operably connected to the cannula mount 324 and provides the second force source upon releasing compression. In an implementation, the helical mandrel spring 310 and helical cannula spring 314 are manufactured from 300 series stainless steel. In an implementation, the force source is compressed air, or electromagnetic energy.

Figure 15:
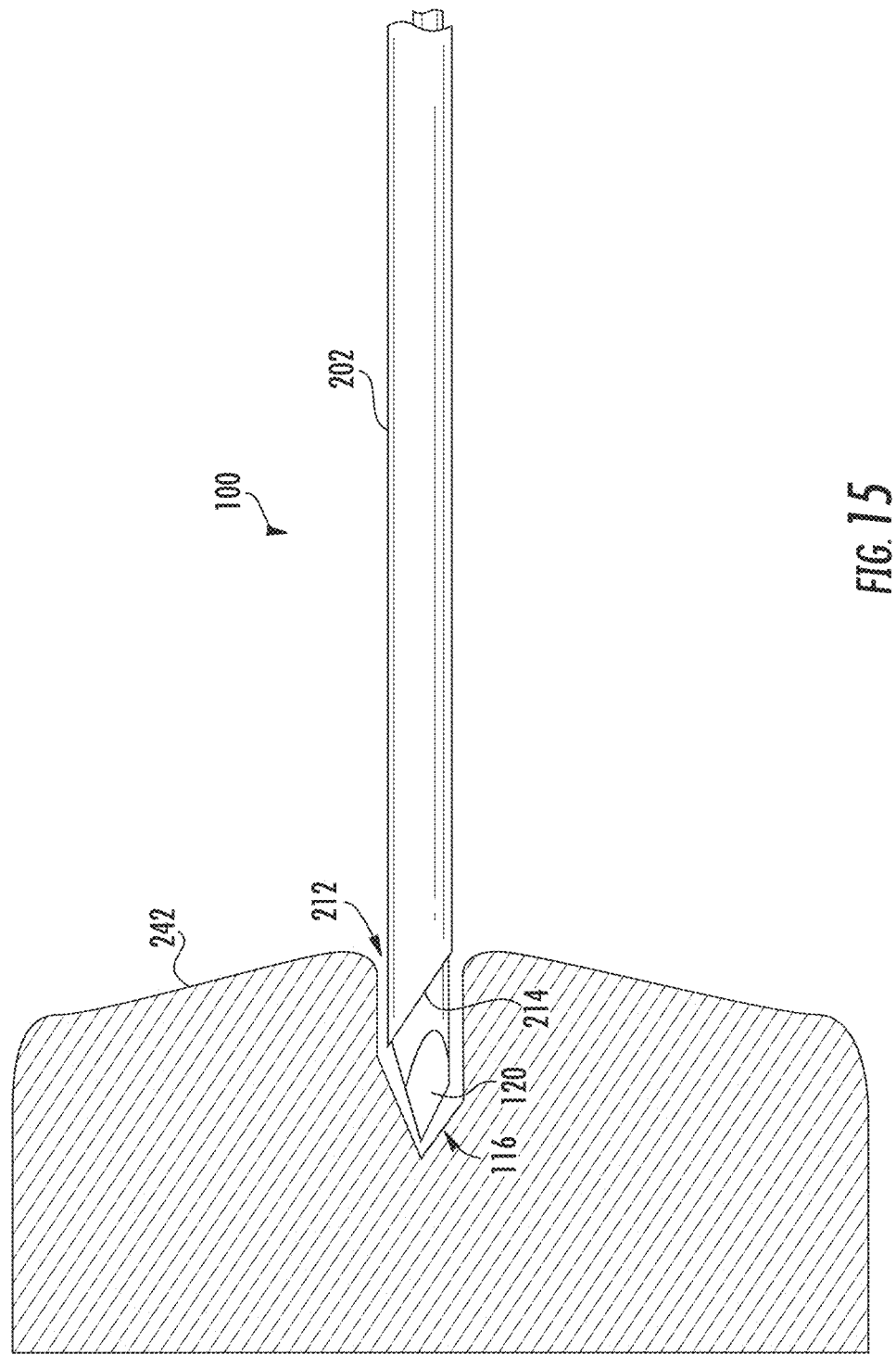
FIG. 15 is an elevation view of a needle assembly embodying features of the disclosed subject matter inserted into a target tissue.

Before use, the exemplary actuator assembly 302 is first armed, placing it in a configuration where it can take a tissue sample. The overall length of the mandrel 102 is longer than the overall length of the cannula 200 to allow the mandrel 102 to extend from the cannula 200 to expose the notch 126 beyond the cutting edge 216. As a result, in the armed position, the mandrel 102 is positioned within a cannula 200 whereby the point 116 protrudes from the first end 204, and the second end 108 is spaced from the second end 206. Referring to FIG. 10, the mandrel carrier 304 is in a first position compressing the mandrel spring 310, and the cannula carrier 306 is in a first position compressing the cannula spring 314. With the carriers 304, 306 in their first positions, the needle assembly 100 is ready for use and the point 116 is advanced to a target tissue 252 (FIG. 15). The target tissue 252 may be any animal tissue desired to be sampled, including human tissue, such as mammalian prostate, kidney, or lung tissue.

Figure 12:
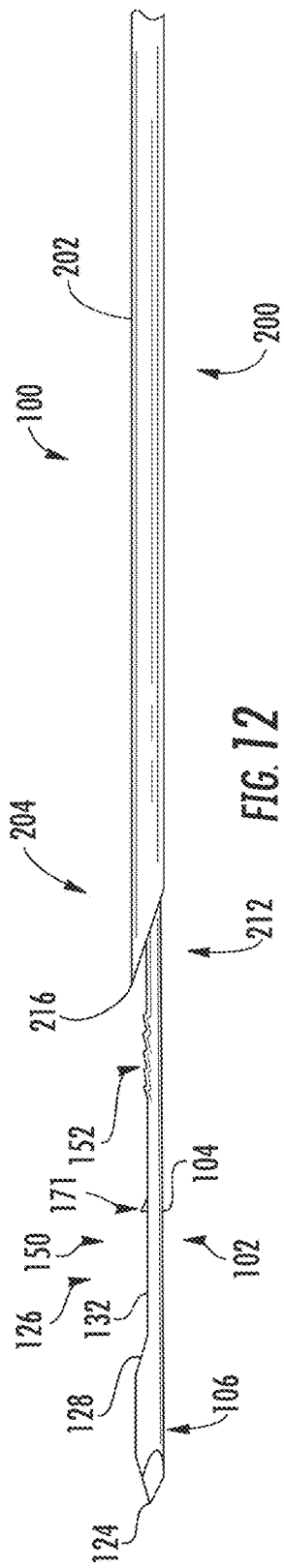
FIG. 12 is a needle assembly embodying features of the disclosed subject matter exposing a first sample region beyond a cannula tip.
Figure 13:
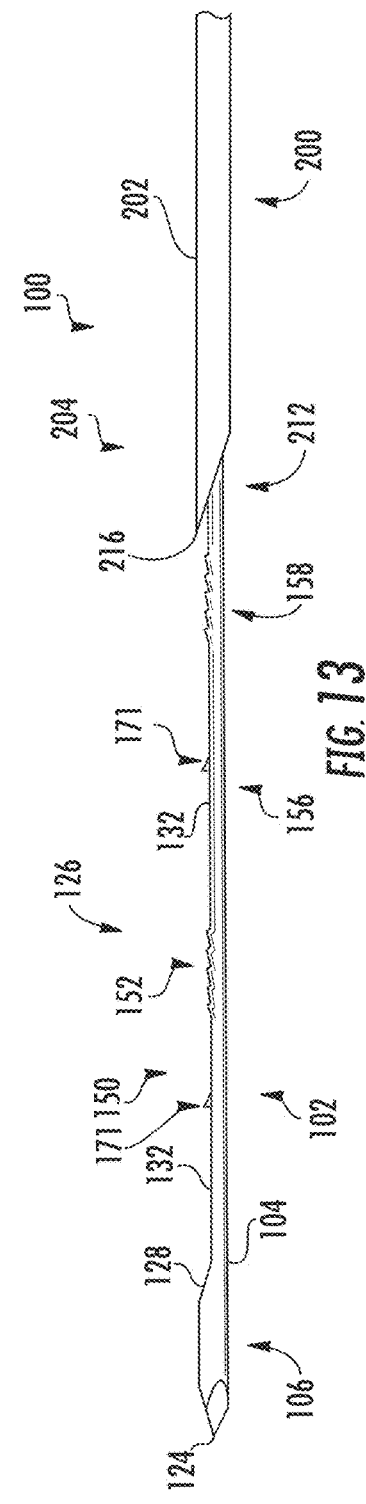
FIG. 13 is a needle assembly embodying features of the disclosed subject matter exposing a first sample region and a second sample region beyond a cannula tip.
Figure 14:
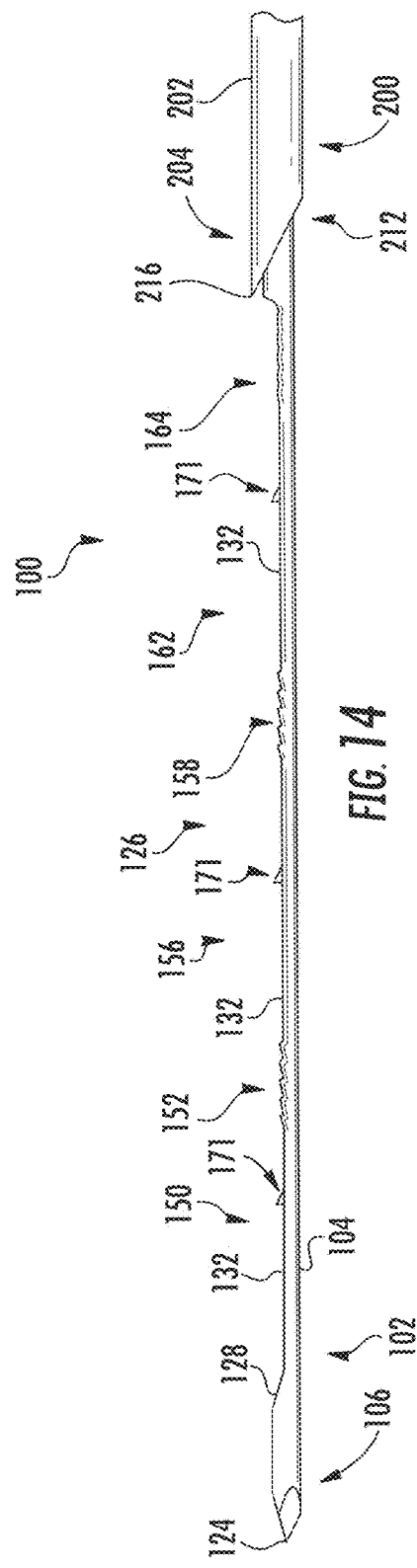
FIG. 14 is a needle assembly embodying features of the disclosed subject matter exposing a first sample region, a second sample region, and a third sample region beyond a cannula tip.

In the exemplary embodiment, removing a first retainer 322 allows the mandrel mount 318 to move forward from a first position to a second position as the mandrel spring 310 decompresses until the front wall 320 of the mandrel mount 318 contacts the stop 308, arresting forward movement of the mandrel 102 and exposing the notch 126 beyond the tip 212. The distance the mandrel 102 moves between the first position and second position, or throw, can be varied to control the length of the notch 126 exposed beyond the tip 212, from between approximately 1 mm to approximately 60 mm. In an implementation, the throw is set whereby the first sample region 150 is exposed beyond the tip 212, exposing approximately 20 mm of the notch 126 (FIG. 12). In an implementation, the throw is set whereby the first sample region 150 and second sample region 156 is exposed beyond the tip 212, exposing approximately 40 mm of the notch 126 (FIG. 13). In an implementation, the throw is set whereby the first sample region 150, second sample region 156, and third sample region 162 is exposed beyond the tip 212, exposing approximately 60 mm of the notch 126 (FIG. 14). Upon firing the mandrel 102 decompression of the spring 310 moves the point 116 into the target tissue 252 exceeding the modulus of elasticity of the target tissue 252, cutting the target tissue 252 and creating a void for passage of the body 104.

Figure 16:
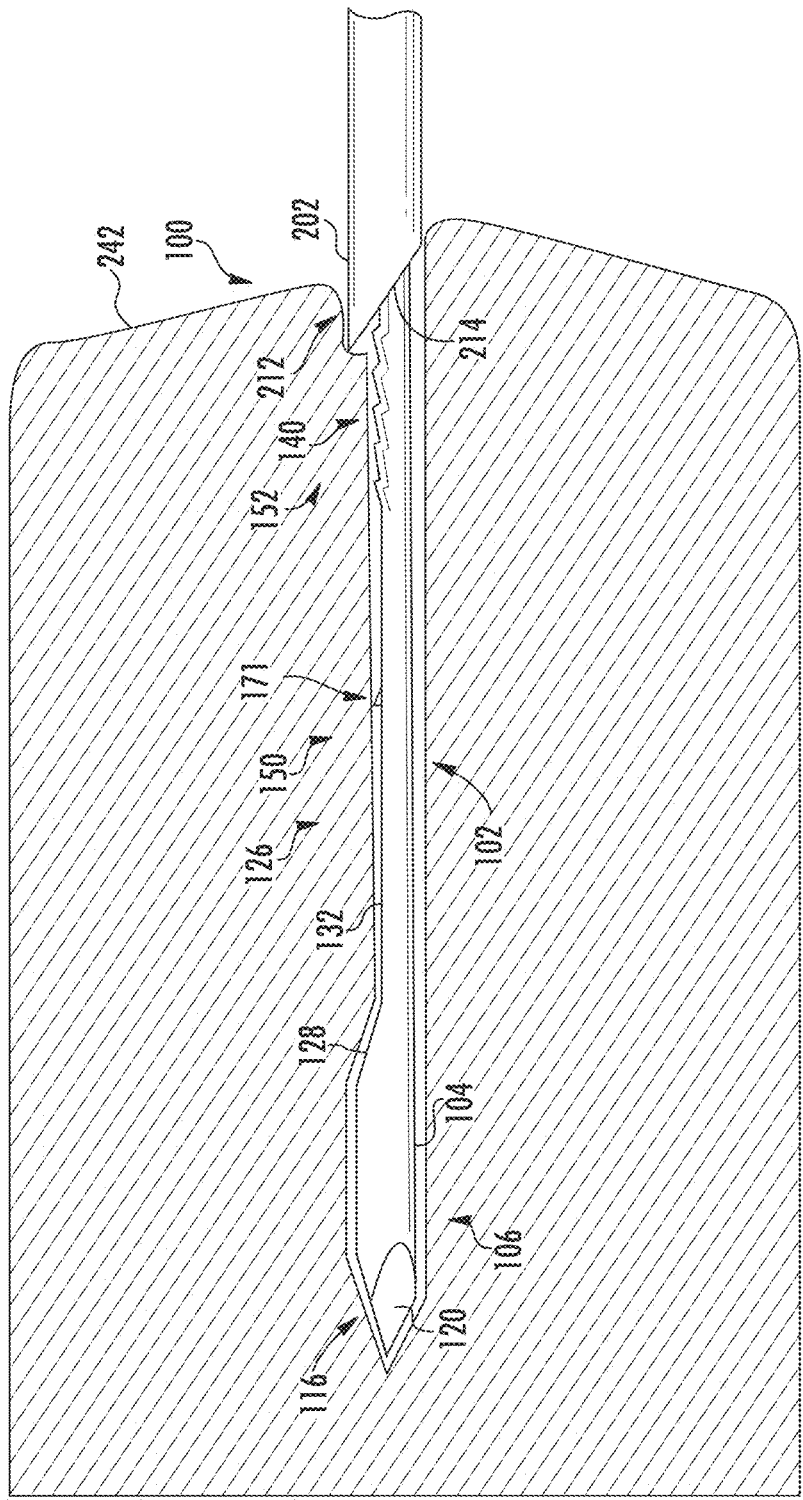
FIG. 16 is an elevation view of the needle assembly of FIG. 15 extending a mandrel into the target tissue exposing a first sample region beyond a cannula tip.
Figure 17:
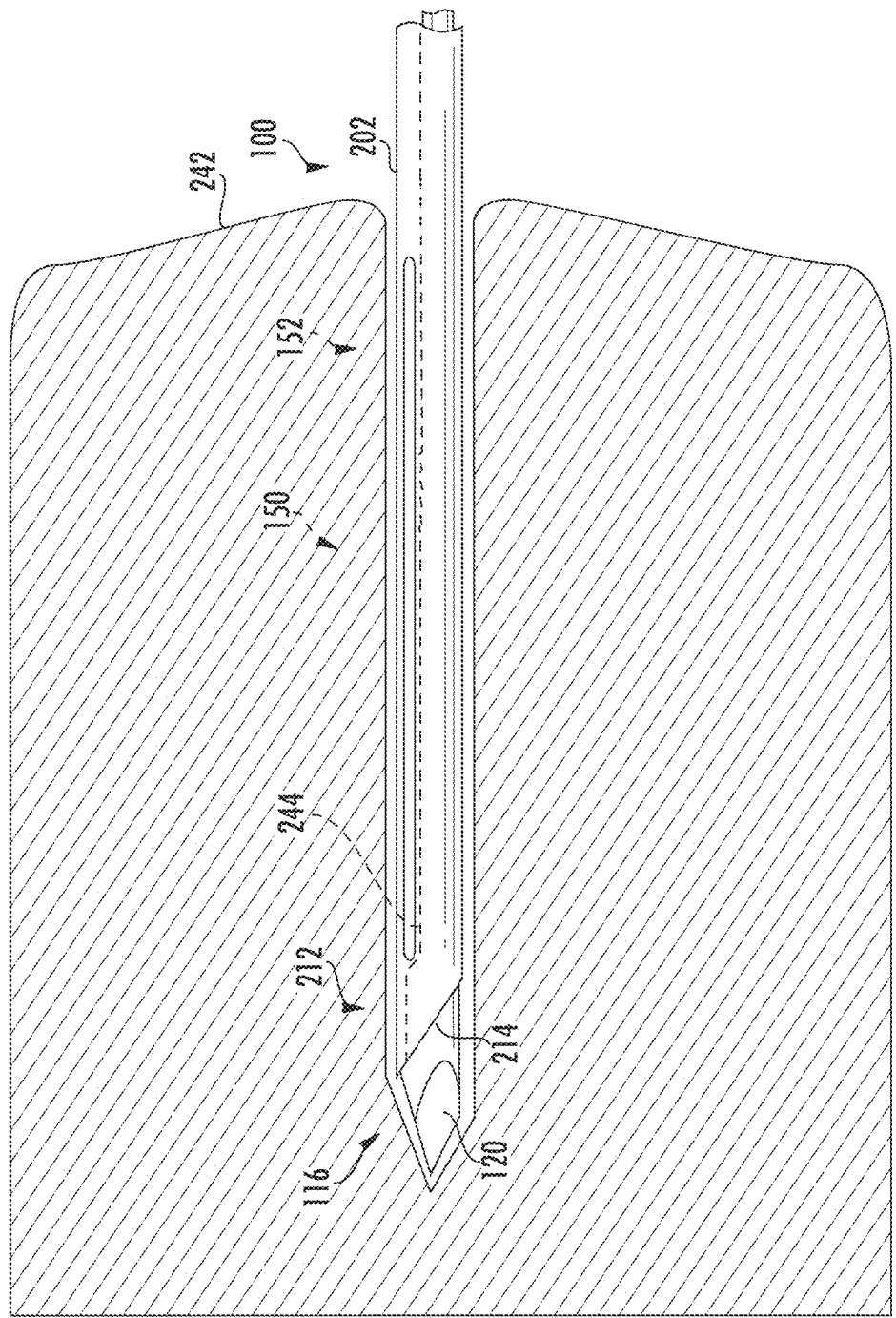
FIG. 17 is an elevation view of the needle assembly of FIG. 15 extending the mandrel into the target tissue and a cannula extending over the first sample region capturing a tissue sample from the target tissue.

Referring to FIG. 16, the first sample region 150 extends beyond the tip 212. When the exposed notch 126 comes to rest in the target tissue 252, the tissue around the notch 126 relaxes, moving into the notch 126. Referring to FIG. 17, the cannula 200 is then fired to cut and separate the tissue sample from the target tissue 252. Removing the second retainer 328 allows the cannula mount 324 to move from the first position forward to a second position as the cannula spring 314 decompresses. The ridges 140 exposed beyond the tip 212 make contact with the target tissue 252, and as the cannula 200 moves from the first position to a second position the ridges 140 engage the sample tissue 252 and limit movement of the tissue within the notch 126 toward the first end 106 as the cannula 200 inner circumferential surface 224 moves across the sample tissue 252. The cannula mount 324 moves toward the stop 308 until the front wall 326 contacts the stop 308, arresting forward movement of the cannula 200. The throw distance of the cannula 200 is set consistent with the throw distance for the mandrel 102 so that the cannula 200 cuts the tissue sample 254 for the target tissue 252 retaining the tissue sample 254 within the notch 126.

In an implementation, the actuator assembly 302 is armed whereby the mandrel mount 318 remains in the second position and the cannula mount 324 is moved to the first position, compressing the helical cannula spring 314 and exposing the notch 126 beyond the tip 212. The mandrel 102 is then inserted into the target tissue 252 and the tissue around the notch relaxes, moving into the notch 126. The cannula 200 is then fired, capturing a tissue sample 254 within the notch 126.

Figure 18:
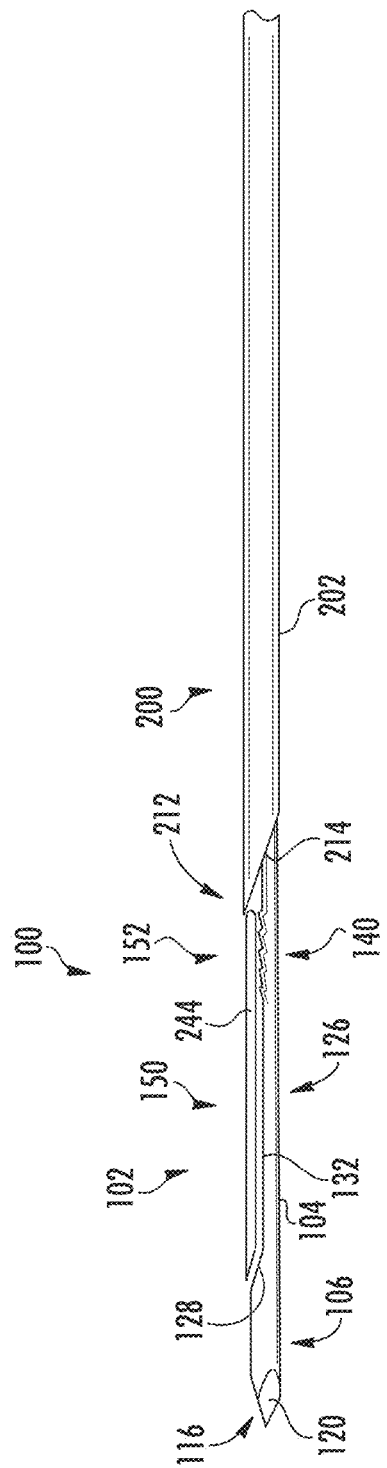
FIG. 18 is an elevation view of the needle assembly of FIG. 15 removed from the target tissue exposing the first sample region beyond the cannula tip and the tissue sample within the first sample region.

After the cannula 200 is fired, the tissue sample 254 is captured within the notch 126 between the cannula 200 inner circumferential surface 224 and bed 132 (FIG. 17). The needle assembly 100 is removed from the target tissue 252 and the tissue sample 254 is removed from the notch 126 by either moving the cannula 200 from the second position to the first position (FIG. 18), or by further decompressing the spring 310 and advancing the mandrel 102 to a third position whereby the notch 126 is exposed beyond the first end 204 of the cannula 200. The reverse ridges 171 engage the tissue sample 254 and limit movement of the tissue within the notch 126 toward the second end 108 as the cannula 200 inner circumferential surface 224 moves across the sample tissue 252. The ridges minimize tissue sample 254 bunching and fragmentation within the notch 126.

EXAMPLES

Background work was conducted on combinations of mandrel point designs, cannula tip designs, and actuator and spring features to evaluate the performance characteristics of the disclosed subject matter in the excision of extended length biopsy core samples of target tissues.

Example 1

A deflection analysis was conducted on various needle designs. Five biopsy needle assembly designs were tested: 1) an 18 gauge lancet-tip mandrel/needle and complimentary cannula used with the Bard® Monopty® device; 2) a 15 gauge lancet-tip mandrel/needle with a 12 degree vet-point cannula; 3) a 15 gauge trocar-tip mandrel/needle with a 12 degree vet-point cannula; 4) a 15 gauge trocar-tip mandrel/needle with a 15 degree vet-point cannula; and 5) a 15 gauge trocar-tip mandrel/needle with a 20 degree vet-point cannula. Each of the 15 gauge mandrels were designed with a notch length fixed at 60 mm to be used with a cannula to collect a variable biopsy core specimen length between approximately 1 mm and approximately 60 mm.

The 18 gauge Bard® mandrel has a needle diameter of 1.0 mm, a notch depth of 0.56 mm, and a notch length fixed at 20 mm, providing a tissue volume within the notch of approximately 0.00055 $cm^3$ when excising a 20 mm tissue sample length. The 15 gauge mandrel has a needle diameter of 1.5 mm, a notch depth of 0.76 mm, and a notch length fixed at 60 mm. The 15 gauge mandrel provides a tissue volume within the notch of approximately 0.0011 $cm^3$ when excising a 20 mm tissue sample length. The 15 gauge mandrel provides a tissue volume within the notch of approximately 0.0033 $cm^3$ when excising a 60 mm tissue sample length.

The five needle assembly designs were tested on a test fixture and fired in a first direction into a gelatin matrix approximating a target tissue with a modulus of elasticity similar to human prostate (a gelatin at 4.0% by mass to water resulting in an average elastic modulus of 3.6 psi). Each of the 15 gauge mandrel and cannula assemblies were tested to excise a tissue sample length of 20 mm, 40 mm, and 60 mm. High-speed images of the mandrel entry and resting positions were captured to determine deflection angle and penetration distance.

Figure 19:
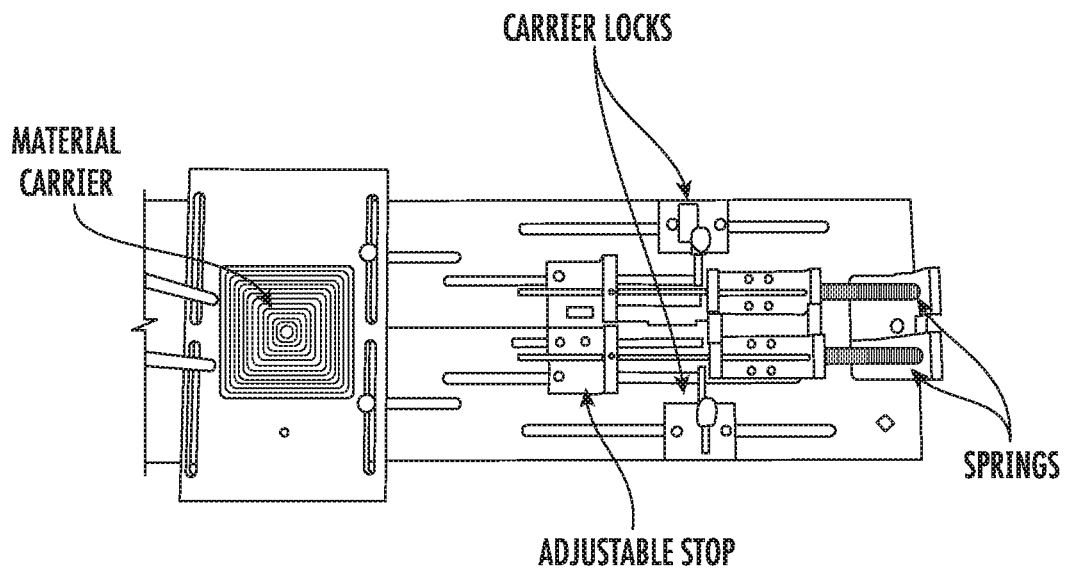
FIG. 19 is a photograph of a breadboard type test fixture.

Each mandrel and cannula were loaded into carriers on a breadboard type test fixture and the needle assembly was secured in place (FIG. 19). The carriers are actuated by compression springs to fire the mandrel and cannula in the first direction into the gelatin matrix. The springs were preloaded by compression and carrier locks were set to maintain spring preload prior to firing. The fixture was set for the needle assembly to take the specified shot length by adjusting the distance the carriers travel until making contact with a stop, selecting a spring with the desired spring constant, compressing the spring to have a specified preload force. Upon removal of the carrier locks, movement of the mandrel and cannula into the gelatin matrix was arrested by an adjustable stop on the test fixture.

The gelatin matrix was positioned in the test fixture and punctured by the tip of the needle assembly prior to firing the needle assembly.

High-speed images of the entry positions of the needle assemblies, firing of the needle assemblies, and resting position of the needle assemblies were captured. The gelatin matrix was replaced after firing the needle assembly into the matrix nine times.

Images of the mandrel deployed into the gelatin matrix and the cannula retracted were isolated. The deflection distance and angle were determined by drawing a first reference line along the bottom of the cannula outside of the gelatin matrix, and drawing a second reference line tangent to the bottom of the mandrel beginning at the distal end of the mandrel, reflecting the greatest deflection. The angle between the two line segments was measured. Linear deflection was determined using the measured angle and the sum of the shot and 6 mm tip length (i.e. (shot length+6 mm)× tangent (measured deflection angle)). The results are reflected in Table 1 (FIGS. 20A-20B).

Figure 21:
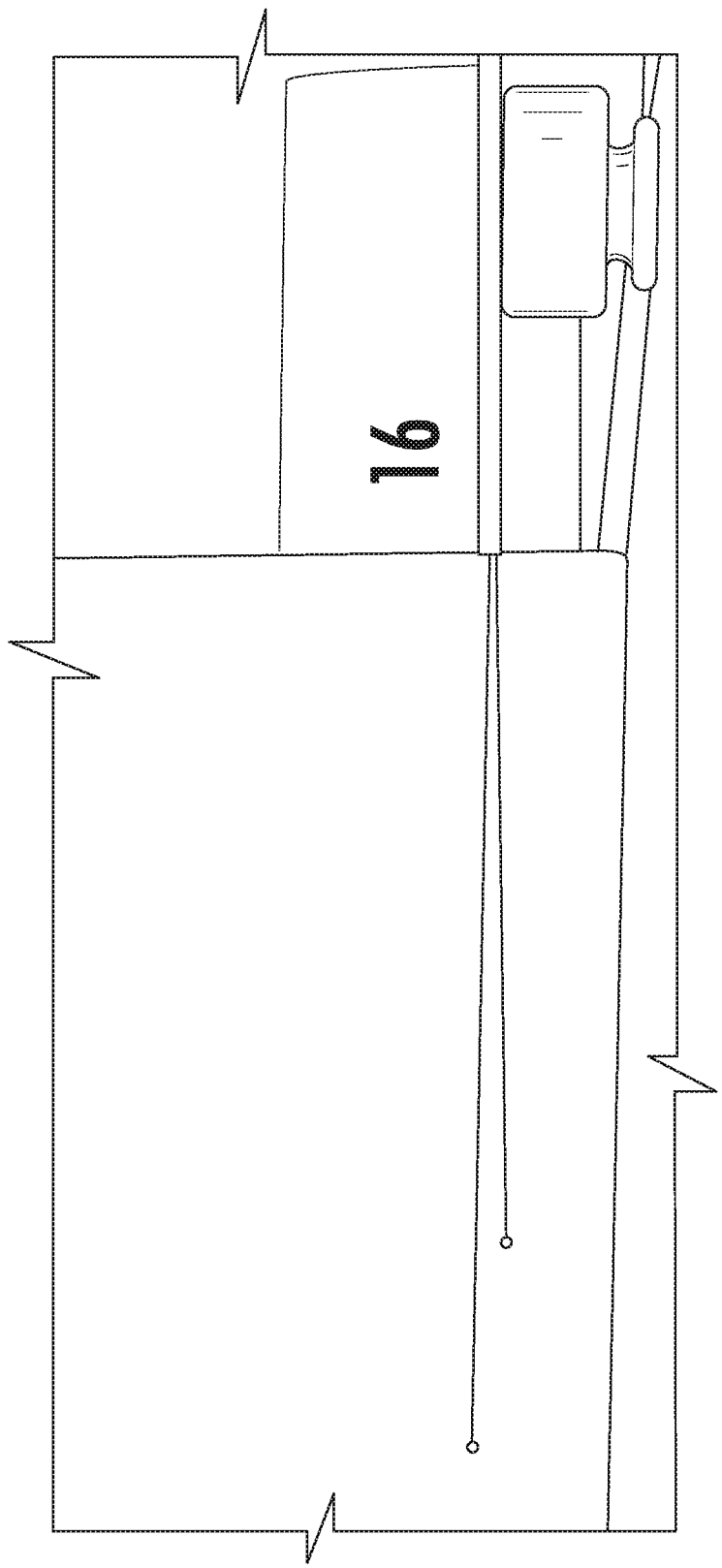
FIG. 21 is a photograph of a needle deployed into gelatin matrix.
Figure 22:
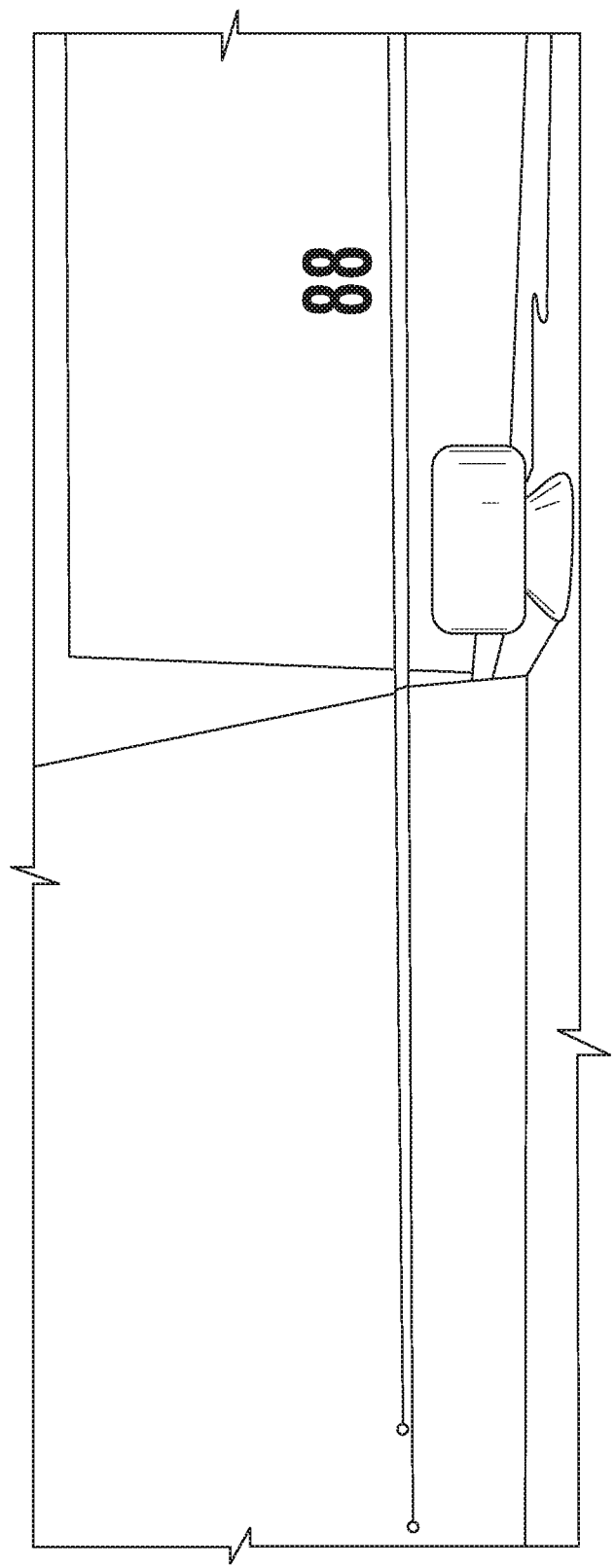
FIG. 22 is a photograph of a needle deployed into gelatin matrix.

The difference in deflection between the 15 gauge mandrel with a lancet-tip versus a 15 gauge mandrel with a trocar-tip is reflected in FIGS. 21 and 22. FIG. 21 shows the result of test no. 16 in Table 1, demonstrating the 2.0 degree deflection of a 15 gauge lancet-tip needle with a 15 degree vet-tip cannula, each fired 40 mm. FIG. 22 shows the result of test no. 88 in Table 1, demonstrating no deflection of a 15 gauge trocar-tip needle with a 20 degree vet-tip cannula, each fired 60 mm.

The Bard® needle system deflected an average of 0.9 mm (range 0.3-1.3 mm) and an average of 1.9 degrees (range 0.6-2.8 degrees). The 15 gauge lancet-tip mandrel with a 12 degree vet-point cannula had an average deflection across the three test lengths of 0.9 mm (range 0-2.0 mm) and 0.9 degrees (range 0-2.0 degrees). Statistical analysis demonstrated no significant differences between the Bard® 18 gauge lancet-tip mandrel and cannula, and 15 gauge lancet-tip mandrel with a 12 degree vet-point cannula (p=0.671 and 0.064) (Table 2). The 15 gauge trocar-tip mandrels had significantly decreased deflection. No deflection was observed at 20 mm and 40 mm core lengths for needle assemblies with the 15 gauge trocar-tip mandrel used in conjunction with the 12 degree vet-point cannula, the 15 degree vet-point cannula, and the 20 degree vet-point cannula. At the 60 mm core length with the 15 gauge trocar-tip mandrel and the 20 degree vet-point cannula, the needle assembly had 0 degrees of deflection when fired using a spring with a spring rate of 2 lbs./in. and a preload of 2.5 lbs.

TABLE 2

| Needle | Cannula | No. of Tests | Mean (mm) | Mean (°) | Difference (p-value) |
|---|---|---|---|---|---|
| Bard ® | Bard ® | 8 | 0.9 | 1.9 | Reference |
| Lancet Point | Vet Point, 12° | 9 | 0.9 | 0.9 | 0.671/0.064 |
| Trocar | Vet Point, 12° | 18 | 0.3 | 0.3 | 0.033/0.002 |
| Trocar | Vet Point, 15° | 17 | 0.2 | 0.1 | 0.013/0.002 |
| Trocar | Vet Point, 20° | 18 | 0.2 | 0.2 | 0.000/0.000 |

The trocar-tip needle assemblies demonstrated significant reduction in the extent of deflection in both millimeters and degrees compared to the Bard® needle assembly. The trocar-tip mandrel design combined with a vet-point cannula significantly reduces deflection over the lancet-tip mandrel design.

Example 2

Further deflection analysis were conducted on various needle designs evaluating cannula geometry, spring rate, and spring preload. Two cannula tip designs, a 12 degree vet-tip grind and a 20 degree Meninghi-tip grind, were tested against the 18 gauge mandrel/needle used with the Bard® Monopty® device to sample tissues between approximately 20 mm and 60 mm in length. The vet-tip cannula has a straight bevel grind while the Menghini-point had an atraumatic sharpened cannula. 15 gauge trocar-tip mandrels/needles were used with the two cannula tip designs, and ridges were incorporated into the core bed of the mandrel to investigate retention of the tissue specimen within the notch after firing the cannula. The core bed was divided into a first sample region, a second sample region, and a third sample region. The first sample region extended from the distal end of the core bed toward the proximal end of the core bed approximately 20 mm, terminating in a section of ridges. The second sample region extended proximally from the first sample region approximately 20 mm, terminating in a section of ridges, and the third sample region extended proximally from the second sample region approximately 20 mm, terminating in a section of ridges.

As with Example 1, the 18 gauge Bard® mandrel has a needle diameter of 1.0 mm, a notch depth of 0.56 mm, and a notch length fixed at 20 mm, providing a tissue volume within the notch of approximately 0.00055 cm$^3$ when excising a 20 mm tissue sample length. The 15 gauge mandrel has a needle diameter of 1.5 mm, a notch depth of 0.76 mm, and a notch length fixed at 60 mm. The 15 gauge mandrel provides a tissue volume within the notch of approximately 0.0011 cm$^3$ when excising a 20 mm tissue sample length. The 15 gauge mandrel provides a tissue volume within the notch of approximately 0.0033 cm$^3$ when excising a 60 mm tissue sample length.

The mandrel and cannula needle assemblies were loaded into the test fixture (FIG. 19) described in Example 1, allowing for variable core length settings between 20 mm and 60 mm and various spring rates and spring preloads. Porcine kidney was selected as a model target tissue due to its similarity in elastic modulus to human prostate (2.3 psi vs. 2.9 psi). The needle assemblies below were loaded into the carriers, and the carriers were preloaded and fired in the first direction by compression springs into the porcine kidney.

130 test firings were performed with the four needle designs and Bard® needle. The results are reflected in Table 3 (FIGS. 23A-23E). The Bard® needle assembly was fired 10 times with a spring having a spring rate of 4.8 lbs./in., with a preload of 2.6 lbs. to mimic the forces of the Bard® Monopty® device, with target shot sizes of 20 mm, and averaging 15.9 mm. The 15 gauge trocar-tip mandrel with a 12 degree vet-tip cannula was fired with a custom spring from Newcomb Spring Corp., Thornton, Colo., having a spring rate of 2 lbs./in., at a preload of 2.5 lbs., 10 times for each target shot size of 20 mm, 40 mm, and 60 mm, averaging 18.7 mm, 42.6 mm, and 54 mm, respectively. The 15 gauge trocar-tip mandrel with a 12 degree vet-tip cannula was fired with an S-1277 compression spring from Century Spring Corp., Commerce, Calif., having a spring rate of 3.2 lbs./in., at a preload of 3 lbs., 10 times for each target shot size of 20 mm, 40 mm, and 60 mm, averaging 19.4 mm, 37.4 mm, and 57.1 mm, respectively. The 15 gauge trocar-tip mandrel with a 20 degree Menghini-tip cannula was fired with the Newcomb custom spring at a preload of 2.5 lbs., 10 times for each target shot size of 20 mm, 40 mm, and 60 mm, averaging 15.1 mm, 35.4 mm, and 49.1 mm, respectively. The 15 gauge trocar-tip mandrel with a 20 degree Menghini-tip cannula was fired with the S-1277 compression spring at a preload of 3 lbs., 10 times for each target shot size of 20 mm, 40 mm, and 60 mm, averaging 18.9 mm, 32.7 mm, and 47.3 mm, respectively.

Testing of mandrels with ridges resulted in tissue cores approximating the length of the sample region(s) exposed to the porcine kidney. The ridges aid in retention of core samples within the sample region during firing of the cannula, resulting minimal fragmentation of the tissue core sample.

The Bard® 18 gauge needle produced a mean specimen length of 15.9 mm with 93.6% fill. The 15 gauge 12 degree vet-tip with spring rates of 2.0 lbs./in. vs 3.2 lbs./in. across the 3 shot lengths (n=60) yielded 91.6 vs. 90.3% fill (p=0.544). The difference between the two spring rates for the Meninghi-tip needle was 86.3 vs. 84.1% fill (p=0.545). Comparison of the 2.0 and 3.2 lbs. spring rates for the vet-tip versus the Meninghi-tip needles yielded 91.6 vs. 86.3% (p=0.056) and 90.3 vs. 84.1% (p=0.060). When all 60 Vet-tip tests were compared to the 60 Meninghi-tip tests the difference in fill was 91.0 vs. 85.2% (p=0.007). The 15 gauge trocar tip needle with 12 degree vet-tip cannulas utilizing a spring rate of 2 lbs./in., and a preload of 2.5 lbs. had the best performance with an average of 90.1% core fill. The vet-tip needle with the lower spring rate and preload performed more consistently than the higher spring rate needle with a lower % standard deviation, +/−6.4% vs. +/−9.8% of fill, and a smaller range of fills, 81-105% vs. 67-107%. The core fill rates by cannula tip configurations, spring rates, and preloads are reflected in Table 4 below.

TABLE 4

| Needle Assembly | Spring Rate (lbs./in.) | Prelaod (lbs.) | Shot Lengths (mm) | Number | Median Fill (%) | Mean Fill (%) | SD (%) | Mean Range Fill (%) |
|---|---|---|---|---|---|---|---|---|
| Bard ® Monopoty ® | 4.8 | 2.5 | 17 | 10 | 94.1 | 93.6 | 7.3 | 78-100 |

TABLE 4-continued

| Needle Assembly | Spring Rate (lbs./in.) | Prelaod (lbs.) | Shot Lengths (mm) | Number | Median Fill (%) | Mean Fill (%) | SD (%) | Mean Range Fill (%) |
|---|---|---|---|---|---|---|---|---|
| 15 Gauge 12 deg. Vet-tip | 2 | 2.5 | 20-60 | 30 | 90.6 | 91.6 | 6.4 | 85-98 |
| 15 Gauge 12 deg. Vet-tip | 3.2 | 3 | 20-60 | 30 | 93.9 | 90.3 | 7.0 | 87-99 |
| 15 Gauge 20 deg. Menghini-tip | 2 | 2.5 | 20-60 | 30 | 89.3 | 86.2 | 11.0 | 71-100 |
| 15 Gauge 20 deg. Menghini-tip | 3.2 | 3 | 20-60 | 30 | 80 | 84.1 | 12.1 | 69-87 |

Example 3

Performance characteristics for two existing biopsy actuator and needle devices capable of excising tissue samples of no more than 20 mm (Table 5) were compared to three combinations of the mandrel, cannula, and force sources of the disclosed subject matter capable of excising tissue samples of between approximately 1 mm to approximately 60 mm (Table 6) showing the preload force and momentum of firing of the needle assembly associated with each system. Referring to Table 5, the measured values for the Bard® Monopty® system and Inrad system are shown.

As with the exemplary actuator above, each of the mandrel and cannula are fired in the first direction, traveling between a first position and a second position. The springs have spring rates. The preload force is the force generated by the mandrel spring and cannula spring with the associated carriers at their second positions prior to further compression and firing. The loaded force is the force generated by the springs with the associated carriers at their first positions with springs compressed and ready for firing. The mass of the system reflects the mass of the mandrel and associated mandrel carrier, and the cannula and associated cannula carrier. Accordingly, each system then has a stored energy, and upon firing, a resulting velocity and momentum in the first direction associated with the mandrel and cannula for the shortest distance traveled between their first and second positions (in this case, 20 mm), and a momentum in the first direction associated with the longest distance traveled between their first and second positions (in this case, 60 mm).

TABLE 5

|  | Bard ® Monopty ® System | | Inrad System | |
|---|---|---|---|---|
|  | Mandrel | Cannula | Mandrel | Cannula |
| Spring Rate (lb/in.) | 4.64 | 4.64 | 6.1 | 5.5 |
| Preload Force (lbs.) | 2.55 | 2.55 | 3.36 | 3.03 |
| Loaded Force (lbs.) | 6.36 | 6.36 | 10.68 | 9.63 |
| Mass (g) | 3.5 | 2.2 | 5.05 | 4.54 |
| Stored Energy (J) | 0.492 | 0.492 | 1.055 | 0.951 |
| Velocity (m/s) | 16.761 | 21.141 | 20.437 | 20.467 |
| Momentum Shortest (kg m/s) | 0.059 | 0.047 | 0.103 | 0.093 |

Referring to Table 6, the measured values for a standard actuator with metal mandrel and cannula carriers using the spring with a spring rate of 2 lb./in, an actuator with a reduced mass mandrel and cannula carriers using the spring with a spring rate of 2 lb./in, and a standard actuator with metal mandrel and cannula carriers using the spring with a spring rate of 3.2 lb./in are shown.

TABLE 6

|  | Standard Mass and Newcomb Custom Spring System | | Minimum Mass and Newcomb Custom Spring System | | Standard Mass and S-1277 Spring System | |
|---|---|---|---|---|---|---|
|  | Mandrel | Cannula | Mandrel | Cannula | Mandrel | Cannula |
| Spring Rate (lb./in.) | 2 | 2 | 2 | 2 | 3.2 | 3.2 |
| Preload Force (lbs.) | 2.5 | 2.5 | 2.5 | 2.5 | 3 | 3 |
| Loaded Force (lbs.) | 7.32 | 7.32 | 7.32 | 7.32 | 10.68 | 10.68 |
| Mass (g) | 21.6 | 17.85 | 11.5 | 7.75 | 21.6 | 17.85 |
| Stored Energy (J) | 1.504 | 1.504 | 1.504 | 1.504 | 2.015 | 2.015 |
| Velocity (m/s) | 7.633 | 8.396 | 10.460 | 12.742 | 9.178 | 10.096 |
| Momentum Shortest (kg m/s) | 0.165 | 0.150 | 0.120 | 0.099 | 0.198 | 0.180 |
| Momentum Longest (kg m/s) | 0.239 | 0.217 | 0.174 | 0.143 | 0.282 | 0.256 |

The loaded forces were in a range between approximately 7 lbs. to approximately 11 lbs. The momentum for the mandrel was in a range between approximately 0.120 kg m/s to approximately 0.282 kg m/s in the fired or first direction, preferably between approximately 0.165 kg m/s to approximately 0.239 kg m/s. The momentum for the cannula was is a range between approximately 0.099 kg m/s to approximately 0.256 kg m/s in the fired or first direction, preferably between approximately 0.150 kg m/s to approximately 0.217 kg m/s.

The above combinations of mandrel 102, cannula 200, and loaded forces deliver a distinct momentum range for the systems of the disclosed subject matter allowing the needle assembly 100 to obtain optimum tissue sample lengths and mandrel 102 notch 126 fill rates when excising tissue samples of between approximately 1 mm to approximately 60 mm.

The disclosed mandrel 102 and cannula 200 designs, and the spring rates and spring preloads of springs 310, 314 minimize or eliminate needle deflection when used in mammalian tissue, increase the accuracy of tissue sample collection, and increase the amount and quality of tissue collected. The resulting improved accuracy of tissue collection, and amount of tissue collected improves the effectiveness of subsequent targeted focal therapy planning and administration.

As required, detailed aspects of the disclosed subject matter are disclosed herein; however, it is to be understood that the disclosed aspects are merely exemplary of the disclosed subject matter, which may be embodied in various forms. Therefore, specific structural and functional details disclosed herein are not to be interpreted as limiting, but merely as a basis for the claims and as a representative basis for teaching one skilled in the art how to variously employ the disclosed technology in virtually any appropriately detailed structure.

The detailed description includes the disclosure of numerical ranges. Numerical ranges should be construed to provide literal support for claim limitations reciting only the upper vale of a numerical range, and provide literal support for claim limitations reciting only the lower value of a numerical range.

Certain terminology used in the description, and shown in the drawings, is not limiting. For example, up, down, front, back, right and left refer to the disclosed subject matter as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning. Elements of the disclosed subject matter that are connected may be directly connected or may be connected through one or more intervening elements.

Although the invention has been disclosed with reference to various particular embodiments, it is understood that equivalents may be employed and substitutions made herein without departing from the scope of the invention as recited in the claims.

Having described the disclosed subject matter, what is claimed is:

1. An apparatus, comprising:
   a cannula, comprising:
      a body extending between a first end and a second end, the body having a first side and an opposite second side; and
      a leading edge formed by the first end, the leading edge extending along a first plane, the first plane extending between the first side and second side, the first plane forming a leading edge angle between the intersection of the first side and the first plane;
   a mandrel, comprising:
      a body extending between a first end and a second end along a central longitudinal axis;
      a notch formed by the body, the notch forming a bed extending between the first end and the second end;
      a first sample region formed by the bed, the first sample region, comprising:
         a first plurality of ridges, wherein each of the first plurality of ridges comprises:
            a flank extending from the bed toward the mandrel body second end, the flank terminating at a crest; and
            a concave slope descending from the crest;
      a second sample region formed by the bed, the second sample region comprising:
         a second plurality of ridges, wherein each of the second plurality of ridges comprises:
            a flank extending from the bed toward the mandrel body second end, the flank terminating in a crest; and
            a concave slope descending from the crest;
      a deck disposed between the first plurality of ridges and the second plurality of ridges.

2. The apparatus of claim 1, further comprising:
   a cannula force source imparting movement to the cannula; and
   wherein the cannula force source imparts a loaded force between 7 lbs. and 11 lbs.

3. The apparatus of claim 2, wherein the loaded force is 7.32 lbs.

4. The apparatus of claim 2, wherein the cannula force source imparts between 2 lbs./in and 3.2 lbs./in upon the cannula.

5. The apparatus of claim 1, further comprising:
   a mandrel force source imparting movement to the mandrel; and
   wherein the mandrel force source moves the mandrel between 1 mm and 66 mm.

6. The apparatus of claim 5, wherein the mandrel force source imparts a loaded force between 7 lbs. and 11 lbs.

7. The apparatus of claim 1, wherein the bed further comprises:
   a reverse ridge, the reverse ridge comprising:
      a flank extending from the bed toward the first end, the flank terminating at a crest; and
      a concave slope descending from the crest.

8. The apparatus of claim 1, wherein the cannula leading edge angle is between 12 degrees and 20 degrees.

9. The apparatus of claim 1, wherein the cannula and mandrel are mounted to an actuator.

10. The apparatus of claim 1, further comprising:
    a vet tip point formed by the cannula leading edge, and wherein the vet tip point leading edge angle is 12 degrees;
    a trocar point with a first beveled surface formed by the mandrel first end, wherein the first beveled surface forms a first beveled angle between the intersection of the first beveled surface and the central longitudinal axis, wherein the first bevel angel is 15 degrees.

11. The apparatus of claim 1, further comprising:
    a cannula spring imparting movement to the cannula, the cannula spring comprising a loaded force between 7 lbs. and 11 lbs.;
    a mandrel spring imparting movement to the mandrel, the mandrel spring comprising a loaded force of between 7 lbs. and 11 lbs.; and
    an actuator housing the cannula spring and mandrel spring.

12. The apparatus of claim 11, wherein the mandrel spring moves the mandrel between 1 mm and 66 mm.

13. The apparatus of claim 1, further comprising:
a vet tip point formed by the cannula leading edge, and wherein the vet tip point leading edge angle is 20 degrees;
a trocar point with a first beveled surface formed by the mandrel first end, wherein the first beveled surface forms a first beveled angle between the intersection of the first beveled surface and the central longitudinal axis, wherein the first bevel angel is 15 degrees.

14. The apparatus of claim 13, further comprising:
a cannula spring imparting movement to the cannula, the cannula spring comprising:
    a spring rate of 2 lbs./in.; and
    a loaded force of 7.32 lbs.;
a mandrel spring imparting movement to the mandrel, the mandrel spring comprising:
    a spring rate of 2 lbs./in.; and
    a loaded force of 7.32 lbs.;
an actuator housing the cannula spring and mandrel spring.

15. The apparatus of claim 13, wherein the bed further comprises:
a reverse ridge, the reverse ridge comprising:
    a flank extending from the bed toward the first end, the flank terminating at a crest; and
    a concave slope descending from the crest.

16. The apparatus of claim 1, further comprising:
wherein the cannula translates in a first direction; and
a cannula force source imparting movement to the cannula, wherein the cannula includes a momentum between 0.099 kg m/s and 0.256 kg m/s in the first direction.

17. The apparatus of claim 16, wherein the cannula momentum is between 0.150 kg m/s and 0.217 kg m/s in the first direction.

18. The apparatus of claim 17, further comprising:
wherein the mandrel translates in the first direction; and
a mandrel force source imparting movement to the mandrel, wherein the mandrel includes a momentum between 0.120 kg m/s and 0.282 kg m/s in the first direction.

19. The apparatus of claim 18, wherein the mandrel momentum is between 0.165 kg m/s and 0.239 kg m/s in the first direction.

20. The apparatus of claim 1, further comprising:
a cannula spring imparting movement to the cannula, the cannula spring comprising:
    a spring rate of 2 lbs./in.; and
    a preload of 2.5 lbs.

21. The apparatus of claim 1, wherein the first sample region extends between the bed at the mandrel body first end toward the mandrel body second end.

22. The apparatus of claim 21, wherein the first sample region extends 20 mm.

* * * * *